US012567500B2

(12) United States Patent
Seth et al.

(10) Patent No.: US 12,567,500 B2
(45) Date of Patent: Mar. 3, 2026

(54) SYSTEM AND METHOD FOR WORKFLOW MANAGEMENT AND IMAGE REVIEW

(71) Applicant: RAD AI, Inc., San Francisco, CA (US)

(72) Inventors: Rishi Seth, San Francisco, CA (US); Matthew Long, San Francisco, CA (US); Michael Emory, San Francisco, CA (US); John Zarate, San Francisco, CA (US)

(73) Assignee: RAD AI, Inc., San Francisco, CA (US)

( * ) Notice: Subject to any disclaimer, the term of this patent is extended or adjusted under 35 U.S.C. 154(b) by 0 days.

(21) Appl. No.: 18/810,172

(22) Filed: Aug. 20, 2024

(65) Prior Publication Data

US 2024/0412858 A1      Dec. 12, 2024

Related U.S. Application Data

(63) Continuation of application No. 17/649,213, filed on Jan. 28, 2022, now Pat. No. 12,106,850.

(Continued)

(51) Int. Cl.
*G16H 40/00*          (2018.01)
*G16H 10/20*          (2018.01)
(Continued)

(52) U.S. Cl.
CPC ............. *G16H 40/20* (2018.01); *G16H 10/20* (2018.01); *G16H 30/20* (2018.01)

(58) Field of Classification Search
CPC ........ G16H 40/00; G16H 10/00; G16H 40/20; G16H 10/20; G16H 30/20; G16H 15/00
See application file for complete search history.

(56) References Cited

U.S. PATENT DOCUMENTS 7,865,371 B2      1/2011   Shen
7,889,896 B2      2/2011   Roehrig et al.
(Continued)

FOREIGN PATENT DOCUMENTS

WO        2011094639 A2      8/2011
WO        2012037049 A2      3/2012
(Continued)

OTHER PUBLICATIONS

A.A.T. Bui; C. Morioka; J.D.N. Dionisio; D.B. Johnson; U.Sinha; S. Ardekani; R.K. Taira; D.R. Aberle; S. El-Saden; H. Kangarloo, openSourcePACS: An Extendable infrastructure for Med image Management, IEEE Trans on Info Tech in biomedicine (vol. 11, Issue 1,2007 pp. 94-109, Jul. 1, 2012 (Year: 2012).*
(Continued)

*Primary Examiner* — Marilyn G Macasiano
(74) *Attorney, Agent, or Firm* — Jeffrey Schox

(57)          ABSTRACT

A system and method for optimizing radiological workflow management and medical image review is disclosed. A preferred embodiment provides a system interoperable with various RIS and PACS systems and that provides efficient access to information, a dynamic prioritized worklist that constantly changes to address optimize distribution of studies and timely review. The novel system facilitates automated assignment, communication between physicians, technicians and radiologists regarding orders, radiographs, reports and studies. The system analyzes exam data, urgency and pendency times, among other things, to automatically determine an overall priority for each case. Cases are assigned for review in the most efficient time, resulting in optimal turnaround time and improved patient care.

17 Claims, 28 Drawing Sheets

Related U.S. Application Data

(60) Provisional application No. 63/199,850, filed on Jan. 28, 2021.

(51) Int. Cl.
*G16H 30/20* (2018.01)
*G16H 40/20* (2018.01)

(56) References Cited

U.S. PATENT DOCUMENTS

| | | | |
|---|---|---|---|
| 7,895,055 B2 | 2/2011 | Schneider et al. | |
| 8,160,347 B2 | 4/2012 | Chaudhuri | |
| 8,165,426 B2 | 4/2012 | Koenig | |
| 8,370,293 B2 | 2/2013 | Iwase et al. | |
| 8,468,032 B2 | 6/2013 | Van Hoe | |
| 8,924,233 B2 | 12/2014 | Backhaus et al. | |
| 9,276,938 B2 | 3/2016 | Raizada | |
| 9,519,753 B1 | 12/2016 | Gerdeman et al. | |
| 9,558,323 B2 | 1/2017 | Jester et al. | |
| 9,727,935 B2 | 8/2017 | Esposito | |
| 10,430,549 B2 | 10/2019 | Backhaus | |
| 10,764,289 B2 | 9/2020 | Raizada | |
| 10,937,164 B2 | 3/2021 | Steigauf et al. | |
| 11,361,530 B2 | 6/2022 | Tahmasebi Maraghoosh et al. | |
| 11,430,563 B2 * | 8/2022 | Hasley | G16H 40/20 |
| 11,515,020 B2 * | 11/2022 | Vozila | G16H 10/60 |
| 11,600,377 B2 | 3/2023 | Volkar et al. | |
| 11,734,333 B2 | 8/2023 | Innanje et al. | |
| 11,769,584 B2 | 9/2023 | Sin Kwok Wong et al. | |
| 12,002,570 B1 * | 6/2024 | Hernandez | G16H 40/20 |
| 2006/0139319 A1 | 6/2006 | Kariathungal et al. | |
| 2007/0143146 A1 * | 6/2007 | Abraham-Fuchs | G16H 10/20 705/3 |
| 2010/0114597 A1 * | 5/2010 | Shreiber | G16H 10/60 382/128 |
| 2011/0218410 A1 * | 9/2011 | Buisman | G16H 50/30 600/300 |
| 2013/0018674 A1 | 1/2013 | Bedi et al. | |
| 2013/0132104 A1 | 5/2013 | Wood-Salomon et al. | |
| 2013/0151284 A1 | 6/2013 | Cohen-Solal et al. | |
| 2014/0257854 A1 | 9/2014 | Becker et al. | |
| 2014/0358585 A1 | 12/2014 | Reiner | |
| 2017/0091399 A1 | 3/2017 | Jester et al. | |
| 2019/0156921 A1 | 5/2019 | Kohli et al. | |
| 2020/0265946 A1 | 8/2020 | Benjamin et al. | |
| 2020/0379620 A1 * | 12/2020 | Horiuchi | G16H 30/20 |
| 2021/0027884 A1 | 1/2021 | Wood | |
| 2021/0035680 A1 | 2/2021 | Chen et al. | |
| 2021/0174941 A1 | 6/2021 | Mathur et al. | |
| 2021/0182745 A1 | 6/2021 | Esposito | |

FOREIGN PATENT DOCUMENTS

| | | | |
|---|---|---|---|
| WO | 2013036842 A2 | 3/2013 | |
| WO | WO 2017184576 A1 * | 4/2017 | G06F 19/00 |
| WO | 2019104093 A1 | 5/2019 | |
| WO | 2020030545 A1 | 2/2020 | |

OTHER PUBLICATIONS

Camorlinga, S. , et al., "Modeling of workflow-engaged networks on radiology transfers across a metro network", (English), IEEE Transactions on information Technology in Biomedicine (vol. 10, Issue: 2, pp. 275-281), Jul. 1, 2012 (Year: 2012).

Chacko, A. K., et al., Virtual radiology environment for the Great Plains Medical Command.

Halsted, Mark J., et al., "Design, implementation, and assessment of a radiology workflow management system", American Journal of Roentgenology 191.2 (2008): 321-327.

Juluru, Krishna , et al., "Internet-based radiology order-entry, reporting,and workflow management system for coordinating urgent study requests during off-hours", American Journal of Roentgenology 184.3 (2005): 1017-1020.

Law, W. , et al., "ntegrated Automatic Examination Assignment u Reduces Radiologist Interruptions: A 2-Year Cohort Study of 232,022 Examinations", Journal of imaging Informatics in Medicine, 37(1), 25-30, Jan. 9, 2024 (Year: 2024).

Wendler, Thomas , et al., "Workflow management systems in radiology." Medical Imaging 1998: PACS Design and Evaluation:Engineering and Clinical Issues, International Society for Optics and Photonics, vol. 3339, 1998.

* cited by examiner

2131 — Retrieve urgency status

2132 — Determine urgency priority value

2133 — Retrieve elapsed time

2134 — Determine elapsed time priority value

2135 — Retrieve physiology

2136 — Determine physiology priority value

2137 — Calculate study priority number

2138 — Insert study in study list

2139 — Reorder study list

Home

Groups

Credentialing

306

346

348

350

My Credentials

| Full Text Search | |
|---|---|
| Site Name | 🔍 Type of Access |
| Collom and Carney Clinic- College | Full |
| Collom and Carney Clinic- Main | Full |
| Collom and Carney Clinic- Northside | Full |
| Collom and Carney Clinic- Richmond | Full |
| Collom and Carney Clinic- Senior | Full |
| Collom and Carney Clinic- Urology | Full |
| Collom and Carney Clinic- Westside | Full |
| Columbia Medical Center | Full |
| Complete Care - Camp Bowie | Full |

352

Credentials By Site

Arlington Memorial Hospital

| Full Text Search | |
|---|---|
| Name | 🔍 Type of Access |
| Adraktas, Dionesia | View |
| Akerley, Brilyn | View |
| Alexander, Ryan | Full |
| Alexander, Tom | Full |
| Alian, Ali | Full |
| Amonette, Shannon | Full |
| Anderson, Carla | View |
| Andrews, Eric | View |
| Andring, Brice | View |

658 — PRIOR STUDIES (33)

660

| CT | MR | US | XR | XA | MG | NM |

|  | DATE | | MOD | EXAM | SITE | ACCESSION | STATUS |
|---|---|---|---|---|---|---|---|
| ⊙ ▫▫▫ | 01/10 | 10:52AM | MR | MRI Brain W/WO | HFW | HF302030 | Final |
| ⊙ ▫▫▫ | 01/10 | 10:52AM | MR | MRI Brain W/WO | HFW | HF302030 | Final (add) |
| ⊙ ▫▫▫ | 01/10 | 10:52AM | MR | MRI Brain W/WO | HFW | HF302030 | Final |
| ⊙ ▫▫▫ | 01/10 | 10:52AM | MR | MRI Brain W/WO | HFW | HF302030 | Final |
| 662 | 664 | | 666 | 668 | 670 | 672 | 674 |

FIG. 6B

| Surname, Name | Exam | SITE | DATE/TIME | |
|---|---|---|---|---|
| Overview | AUDIT HISTORY | | | |
| Demographics | 01/10  10:52 AM | | Order Received | |
| | 01/10  10:52 AM | | Images Received | |
| | 01/10  10:52 AM | | Priority Reviewed | |
| Assignments | 01/12  10:52 AM | TA | Assignment Change | |
| | 01/12  10:52 AM | TA | Priority Change | |
| | 01/12  10:52 AM | TA | Assignment Change | |
| Audit | 01/12  10:52 AM | MD | View / Dictate Assignment Change | |
| | 01/12  10:52 AM | MD | Assignment Change | |
| DICOM Send | 01/12  10:52 AM | MD | Closed in viewer, Closed in dictation | |
| | 01/12  10:52 AM | MD | View / Dictate | |
| | 01/12  10:52 AM | MD | Dictate | |
| | 01/12  10:52 AM | MD | Closed in viewer, Closed in dictation | |
| | 01/12  10:52 AM | | Final | |

SYSTEM AND METHOD FOR WORKFLOW MANAGEMENT AND IMAGE REVIEW

CROSS-REFERENCE TO RELATED APPLICATIONS

This application is a continuation of U.S. application Ser. No. 17/649,213, filed 28 Jan. 2022 which claims priority benefit from U.S. Provisional Application No. 63/199,850, filed on Jan. 28, 2021. The patent application identified above is incorporated here by reference in its entirety to provide continuity of disclosure.

FIELD OF THE INVENTION

The technical field of the invention relates to an automated workflow management system which dynamically optimizes radiological image review.

BACKGROUND OF THE INVENTION

Radiology and the interpretation of radiographs are important tools for the diagnosis and treatment of injury and disease in modern medicine.

The typical radiology process begins with a physician determination that a radiology scan is required. The physician creates a radiology order for a radiology scan. The radiology order is then sent to the radiology technician who performs the radiology scan which produces a set of radiology images. The technician assembles a radiology study, which includes the set of radiology images and the radiology order. The study is then sent to a radiologist for review. The radiologist reads and interprets the images and generates a radiology report. The radiology report is attached to the study and returned to the ordering physician.

In the past, radiology systems were based on radiographic images, or radiographs, were recorded on specialized radiographic film. After exposure, developed film is physically cataloged, stored, and secured. The radiographs require physical organization and tracking. Additionally, the radiographs require physical transportation to and from technicians and radiologists, for reading and interpretation. Physically cataloging, storing and securing radiographs are cumbersome problems that create gross inefficiencies in the radiology process which often interfere with patient care.

Modern radiology systems create and store images as electronic data files, in a database, along with metadata that identifies the type of image and capture date, among other things. Modern radiology systems also allow electronic images to be efficiently stored and transmitted over the internet to different locations. Modern systems often incorporate a Radiology Information System (RIS). A RIS is a computer-based application that typically processes administrative and medical data, such as patient files, scheduling, report management and billing.

Most modern RIS applications often operate in tandem with picture archiving and communication systems (PACS). A PACS typically stores images and related metadata and can electronically transmit them for use with compatible systems.

Typical RIS and PACS systems process data using the Health Level Seven (HL7) and Digital Imaging and Communications in Medicine (DICOM) protocols. These protocols provide international standards for management and communication of medical images and data that ensures certain common formats are used to store, transmit, and display radiographic images across various different vendor platforms.

Storage of modern medical imaging files is typically accomplished through a PACS Archive or a vendor neural architecture (VNA). These archiving systems provide a standard format for long term archiving of digital images and studies and enable consolidation of images from different RIS and PACS systems into a single repository.

Even considering the advances in modern radiology systems, the task of routing radiology studies to radiologists for review remains a challenging task. Radiologists typically specialize in one or more different disciplines, such as neuroradiology, nuclear radiology, pediatric radiology and cardiovascular radiology. Radiologists also typically specialize in various different techniques or "modalities" such as X-ray imaging, computed tomography (CT), magnetic resonance imaging (MRI), positron emission tomography (PET), and ultrasound. Each of the modalities requires different qualifications and credentialling. Differing specialties and qualifications among radiologists limit the types of radiographs they may efficiently review and requires that the studies be sorted before distribution.

Another challenge which remains in modern radiology systems is efficient distribution of electronic images to radiologists in different physical locations with differing schedules. Radiologists are often resident at a single hospital or clinic, even though they review and analyze radiology images from other sources. Similarly, radiologists typically work in different shifts and are "on call" at different times.

Another challenge facing modern systems is timely review of priority orders. Various physical disorders or injuries may require expedited radiological review. Other disorders may require less rapid radiology attention. Routing of radiology studies based on urgency complicates radiology review because expedited cases often replace less urgent cases in queue, delaying the radiology review and forcing reallocation of radiology resources. Likewise, each medical facility generally recommends time limits on the review of images by the radiologist in order to promote efficiency. Differing time limits for image review between facilities often interferes with prioritization of studies by artificially elevating studies for less severe cases over studies for more severe cases.

Similarly, communication between the patient, the physician, the radiologist and the technician presents an ongoing challenge for modern radiology systems. Scheduling of radiological scans requires close coordination between the patient, the physician and the technician. Likewise, replacing incorrect radiographs, emergency communication of radiology orders reports and studies, questions and reprioritization of studies all require rapid and efficient communication of messages to facilitate the radiology process and proper timely treatment.

The prior art has attempted to address these challenges, but has fallen short.

For example, U.S. Publication No. 2013/0018674 to Bedi, et al. discloses a method for managing radiology orders which provides for assigning a radiologist for the study based on scheduling rules and control parameters. A "quality index" is provided which grades each radiologist for an assignment of the study.

Another example, U.S. Pat. No. 9,727,935 to Esposito, discloses a method of obtaining data describing medical image studies from a medical data server, and assigning each for examination based on preferences and the complexity of the medical images.

Yet another example, U.S. Pat. No. 9,558,323 to Jester, et al. discloses a system to manage radiologist workflow, including an interface to distribute medical exams to a work queue.

As another example, U.S. Publication No. 2013/0132104 to Wood-Saloman, et al. discloses a method of assigning image studies to a work list using a set of parameters. The parameters include radiologist specialty and location of the patient.

As another example, U.S. Pat. No. 8,924,233 to Backhaus, et al. discloses a method of forecasting radiologist assignments based on sets of parameters. Parameters for a radiologist are matched to parameters for a medical facility. A schedule is implemented based on a volume of medical requests and resource availability.

Hence, there is a continuing need for a radiology system and method that organizes and optimizes the distribution and review of radiographs and which accommodates resolution of issues with communication, scheduling, report generation, case urgency, and case pendency.

SUMMARY OF THE INVENTION

Disclosed is a system and method for optimizing radiological workflow management and medical image review. A preferred embodiment provides a system interoperable with various RIS and PACS systems and that provides efficient access to information by a dynamic prioritized worklist that constantly changes to optimize distribution of studies for timely review. The novel system facilitates automated assignment, communication between physicians, technicians and radiologists regarding orders, radiographs, reports and studies. The system automatically analyzes exam data, urgency and pendency times, among other things, to determine an overall priority for a constantly evolving set of radiology orders. Cases are assigned for review in the most efficient time, resulting in optimal turnaround time and improved patient care.

The system disclosed provides a significant advantage over the prior art because it enables more efficient review of radiographic images and report generation. The system provides a database workflow management system which strategically assigns radiological studies for efficient review of images and provides a dynamic prioritized workflow. The system comprises a workflow management application which integrates third party software and hardware to allow for voice recorded notes and the review of different types of radiological images such as X-rays, CT, MRI, PET, ultrasound and others. Furthermore, the system automatically integrates data from multiple enterprises and medical imaging providers into a single, consolidated, and universal database. The system assigns studies based on analysis of different data and features of a study to determine urgency, priority, radiologist availability, radiologist credentialing, radiologist sub specialization and then assigns studies to maximize work efficiency and minimize review time. In the preferred embodiment, a list of cases is created based on matching the radiologist, shift responsibility, patient details, and case requirements. The list is constantly updated to elevate urgent studies and aged studies in priority for any given radiologist.

The preferred system also provides an integrated communication system which allows instant contact between physicians, technicians and radiologists and which stores and associates all such communications with the proper radiology study for later review.

BRIEF DESCRIPTION OF THE DRAWINGS

In the detailed description of the preferred embodiments presented below, reference is made to the accompanying drawings.

Figure 1A:
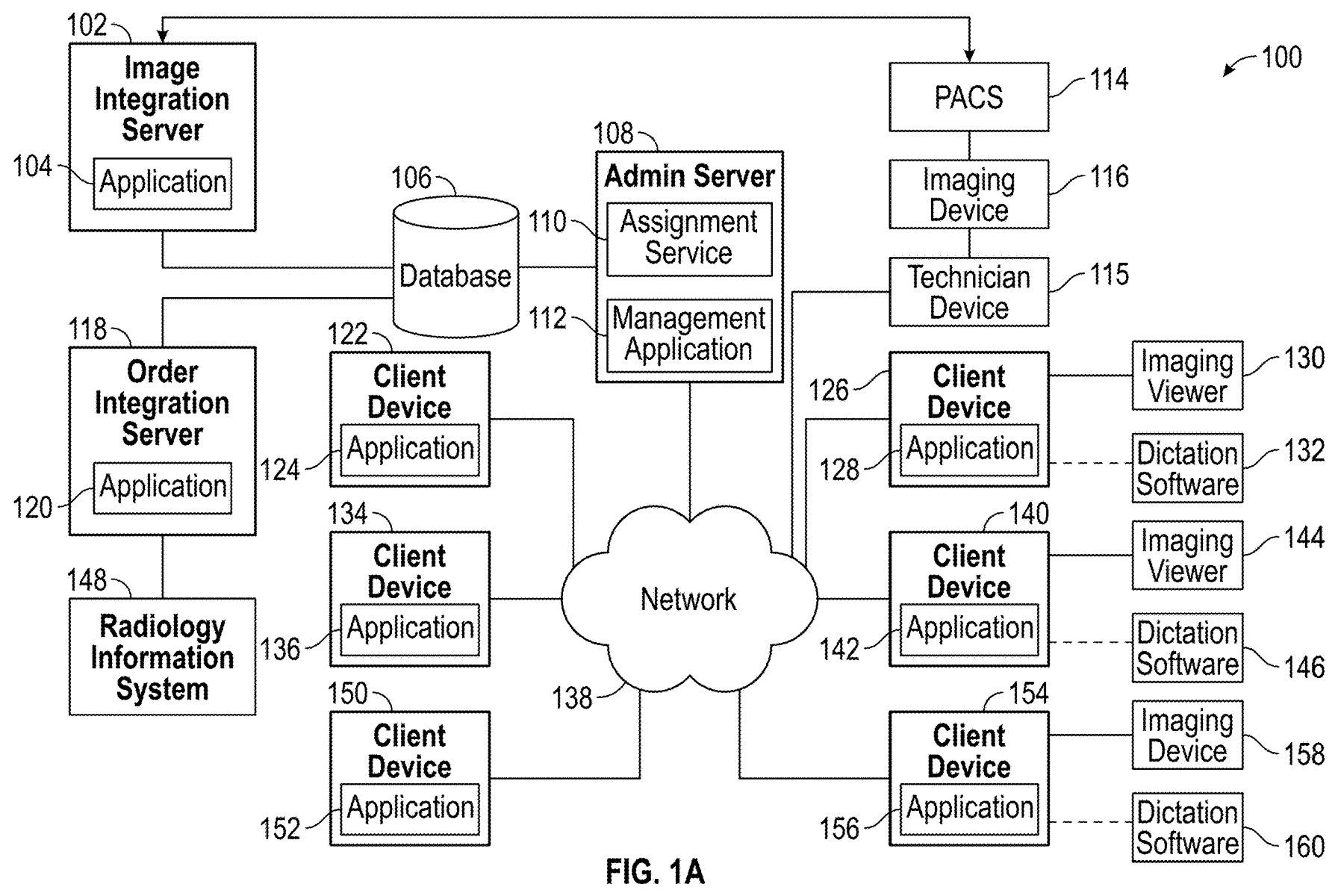

FIG. 1A is architecture diagram of a preferred radiological workflow management system.

FIG. 3C is a screenshot of a graphic user interface for a credentialling the selection of a preferred embodiment.

FIGS. 6B and 6C are screenshots of a graphic user interface of a study summary side panel of a preferred embodiment.

FIG. 9D is a screenshot of a graphic user interface for the audit tab of a preferred embodiment.

DETAILED DESCRIPTION OF THE INVENTION

Figure 1B:
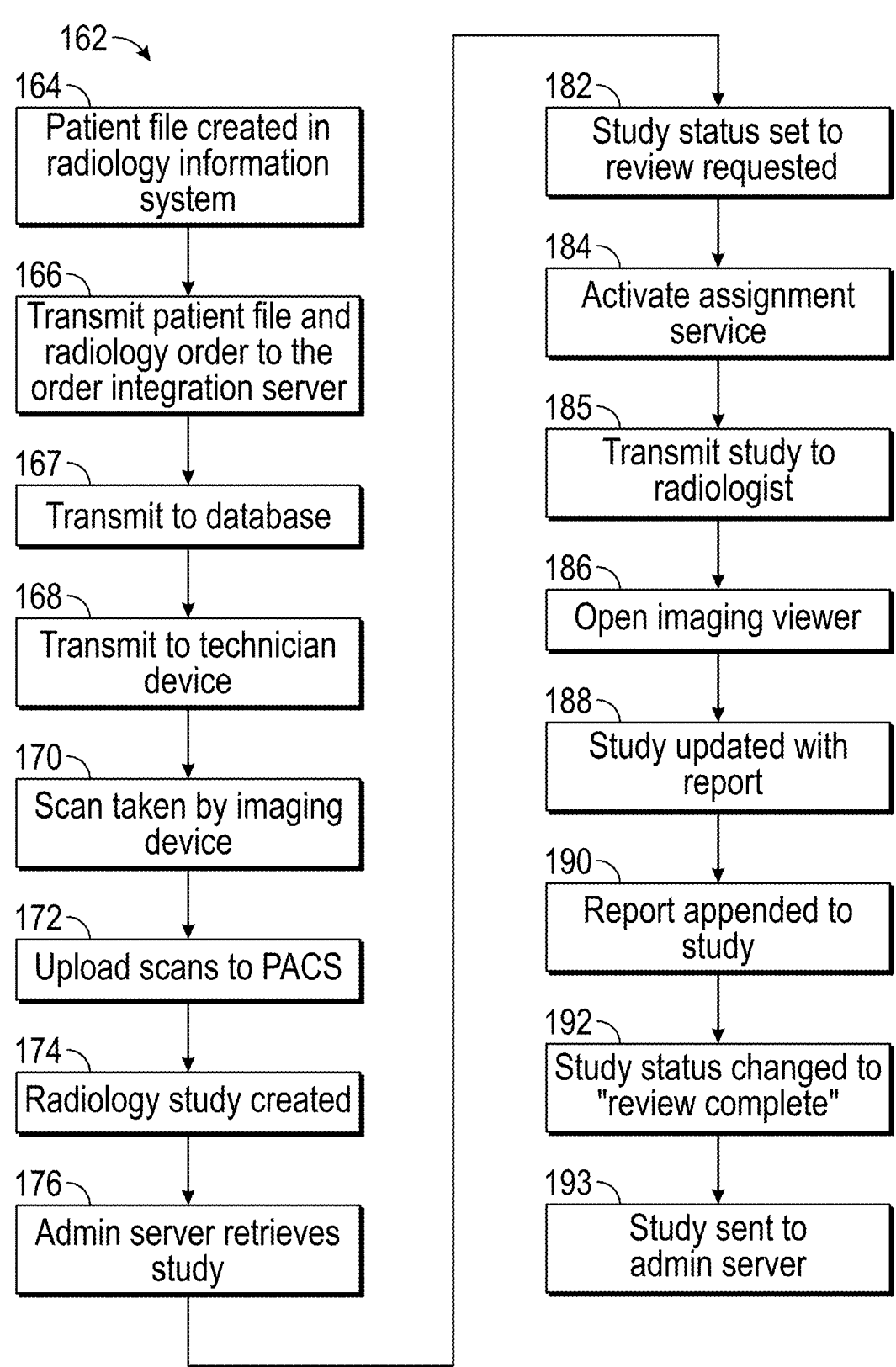
FIG. 1B is a flowchart of a preferred method of workflow management.

In the description that follows, like parts are marked throughout the specification and figures with the same numerals. The figures are not necessarily drawn to scale and may be shown in exaggerated or generalized form in the interest of clarity and conciseness.

Referring then to FIG. 1A, a preferred architecture for system 100 will be described.

System 100 is comprised of multiple servers with supportive software and services which form the workflow management system. Each of the servers is preferably a standalone server and with appropriate processors and memory capable of high-speed communication of large files and radiographic images. In other embodiments, the servers may be implemented as virtual machines resident in the cloud with access provided to users as software as a service.

Administrative server 108 includes assignment service application 110 and management application 112. Assignment service application 110 coordinates location and availability of radiologists with incoming radiology orders, among other things, as will be further described. Management application 112 coordinates communication with various RIS and PACS systems, receipt and processing of image data requests and reports, database queries and worklist generation and updating, as will be further described. Administrative server 108 is operatively connected to database 106 and wide area network 138. Administrative server 108 communicates with database 106 preferably through the DICOM protocol.

Database 106 is preferably a Microsoft SQL server based database system capable of carrying out complex queries and association of images, metadata and associated files required by the study, such as oral dictation files, transcriptions, and associated email storage. A radiologist list and study list are resident on database 106.

The radiologist list is comprised of all radiologist user records. The records include the location, specialty, certifications, work shift, current workload, and current efficiency of each radiologist. The workload and efficiency are automatically updated by the system. The efficiency is calculated as the rate of reviews conducted per hour. The system utilizes advanced SQL queries and code-based algorithms to extract sub lists of radiologists records with specific characteristics to assign studies for review, as will be further described.

The study list is comprised of all the study records. The study records include all information related to the study, such as order number, urgency, patient name, age, injury physiology, location, image type, notes, dictations, preferred radiologist, assigned radiologist, start time, end time, assigned study priority number, any communications between users, and lock out indications, as will be further described. When study images are uploaded into the database they are associated with the appropriate study profile in the database.

In a preferred embodiment, database 106 is further in operative communication with image integration server 102 and order integration server 118.

Image integration server 102 further comprises application 104. Application 104 comprises a VNA system capable of communication with and storage of images from PACS system 114. Preferably PACS system 114 and image integration server 102 communicate through the DICOM protocol.

PACS system 114 is operatively connected to imaging device 116. In a preferred embodiment, imaging device 116 is a third-party radiology imaging device, CT imaging device, X-ray device, or other device capable of recording and transmitting radiographs. In another embodiment, imaging device 116 is a translation device capable of reading and encoding physical radiographs into an electronic format, such as the DICOM format.

Imaging device 116 is operatively connected to technician device 115. Technician device 115 is further operatively connected to network 138. Technician device 115 is responsible for controlling the intake of radiology images from imaging device 116 and communication of those images to PACS system 114 and image integration server 102. Technician device 115 is also responsible for intake and display of data related to the study such as order changes and communications from other services related to the study and the images.

Image integration server 102 is operatively connected with database 106. Preferably, image integration server 102 is capable of retrieving and storing images according to an appropriate database protocol for patient files, according to unique patient IDs and radiology order numbers. Order integration server 118 further comprises application 120. Application 120 is preferably capable of receipt and transmission of radiology orders organized according to a patient ID and a radiology order number.

Order integration server 118 is operatively connected to RIS 148. RIS 148 is responsible for the receipt of radiology orders, storage, organization and communication of those orders to order integration server 118. Order integration server 118 is operatively connected with database 106 and is capable of storing radiology orders in an appropriate format for communication into and from the database.

The system further comprises a plurality of client devices 126, 140, 154, 150, 134 and 122, each connected to administrative server 108 through network 138. Each of the client devices is a smart device, such as a computer, tablet, or cell phone, with applications 128, 142, 156, 152, 136, and 124, respectively, installed. Each of the client devices incorporates appropriate user interfaces, displays, processors and memories sufficient to enable connection with the network and various third party software and hardware to allow creation, viewing and manipulation of radiographic images.

Client devices 126, 140 and 154 are also operatively connected to third-party imaging viewer applications 130, 144, 158 and dictation software 132, 146, 160, respectively. The imaging viewer applications are typically applications associated with specific PACS system 114, and are responsible for reading electronic files and displaying radiographic images.

Referring then to FIGS. 1A and 1B, preferred method of radiology workflow management 162 will be further described.

At step 164, a patient file is created in RIS system 148. The patient file includes patient demographics, physical exam notes, symptoms, medical history and most importantly, the radiology order.

At step 166, the patient file and the radiology order are sent to order integration server 118. At step 167, the patient file and the radiology order are sent to the database.

At step 168, the patient file and the radiology order are retrieved by the administrative server and sent to the technician device through the network. At step 170, radiographic scans of the patient are taken by imaging device 116.

At step 172, the imaging device then uploads the scans into PACS system 114.

At step 174, a radiology study is then created in RIS 148 and transmitted to the administrative server through the order integration server. The radiology study includes the patient file and the scans.

At step 176, administrative server 108 retrieves the study.

At step 182, the study status is set by administrative server 108 to "review requested".

At step 184, the assignment service is initialized by the "review requested" status. The assignment service analyzes the details of the study such as patient symptoms, type of image review requested and urgency. Details extrapolated from the study are used to determine prioritize study and the assigned radiologist, as will be further described. Different factors that determine which radiologist is assigned to a study may include the radiologists' shifts, current worklist, locations, sub-specialties and credentialling. In a preferred embodiment, studies may be reassigned either manually or automatically if certain events occur, such as a radiologist shift change or a time out condition.

At step 185, once a study is assigned, it is transmitted to a radiologist. The radiologist may select a study to review. At step 186, when the study is selected, an imaging viewer, such as imaging viewer applications 130, 144 and 158, opens.

At step 188, a report is added to the study by the radiologist with an analysis of the scans. The analysis may be manually entered into the system, or a third-party voice recognition software, such as dictation software 132, 146 and 160, may be used.

At step 190, the report is appended to the study. At step 192, the study status is then changed to "review complete." At step 193, the study is returned to the administrative server. In a preferred embodiment, when a study has been reviewed, the system updates RIS 148 and a notification is sent to the original office where the order was created to notify the physician.

Referring then to FIGS. 2A, 2B, 2C, 2D, and 2E method 200 for a preferred embodiment of workflow management will be further described.

Figure 2A:
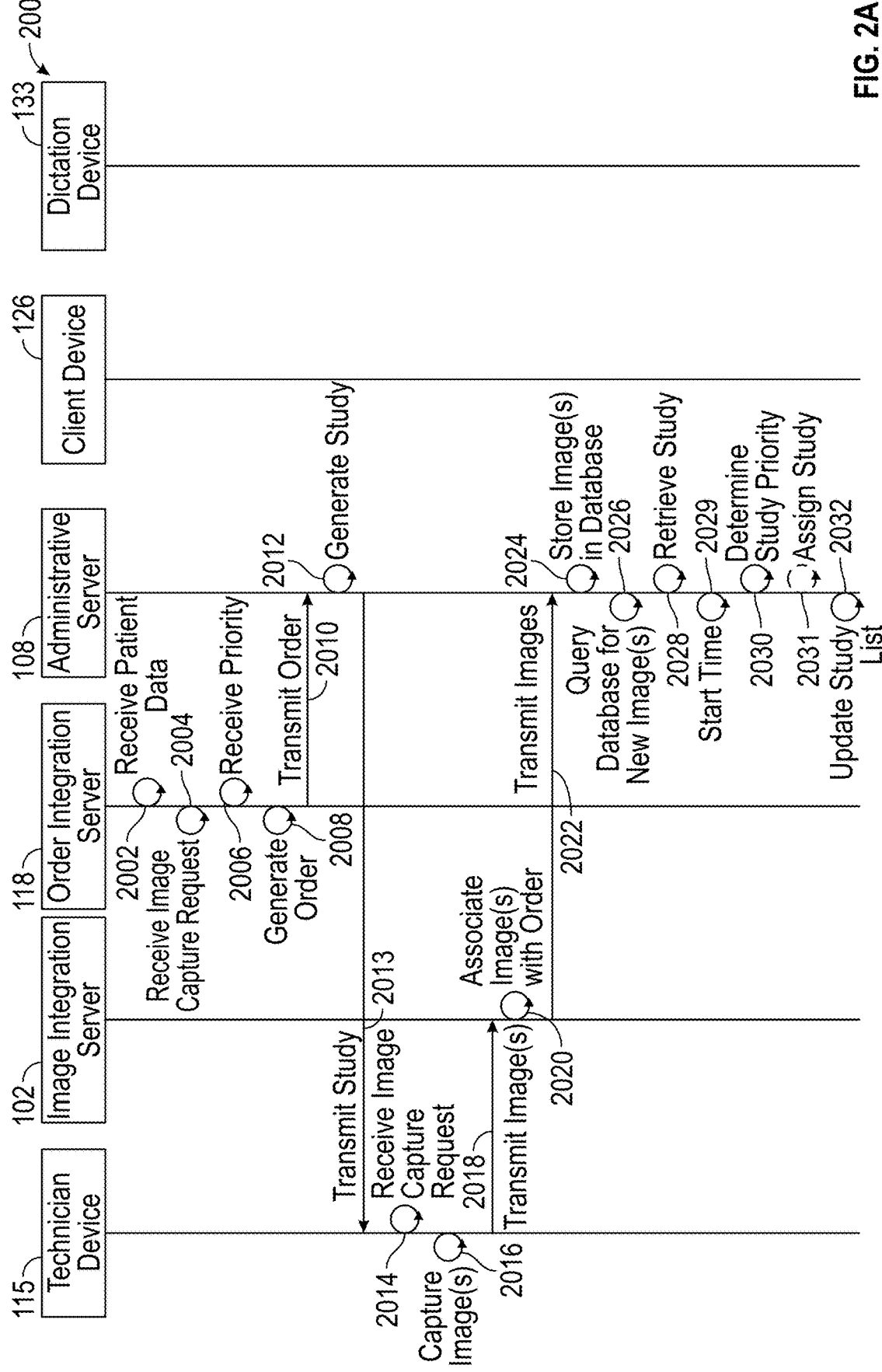
FIGS. 2A, 2B, 2C, 2D, and 2E are a network communication diagram of a preferred embodiment.
Figure 2B:
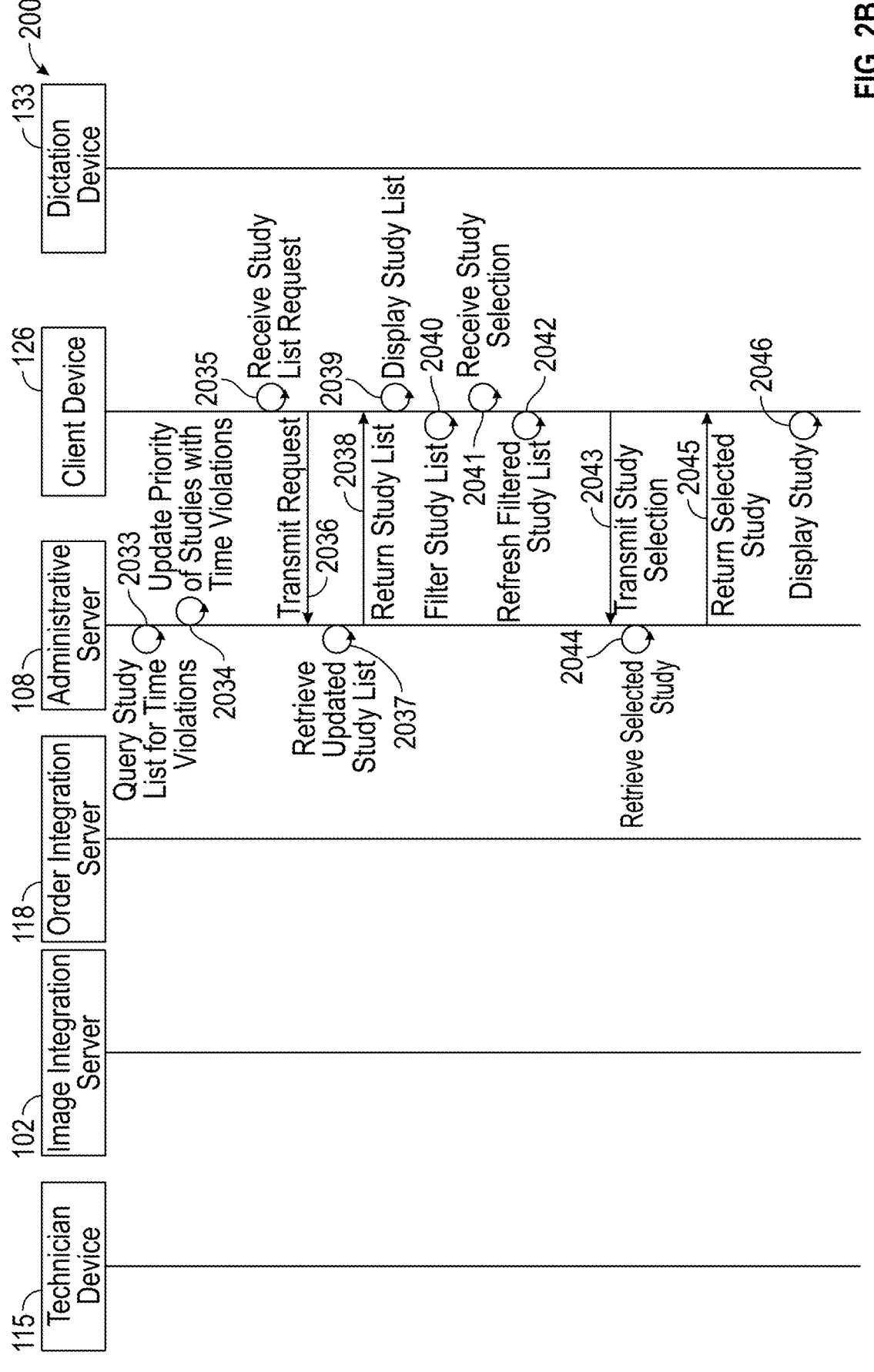
Figure 2C:
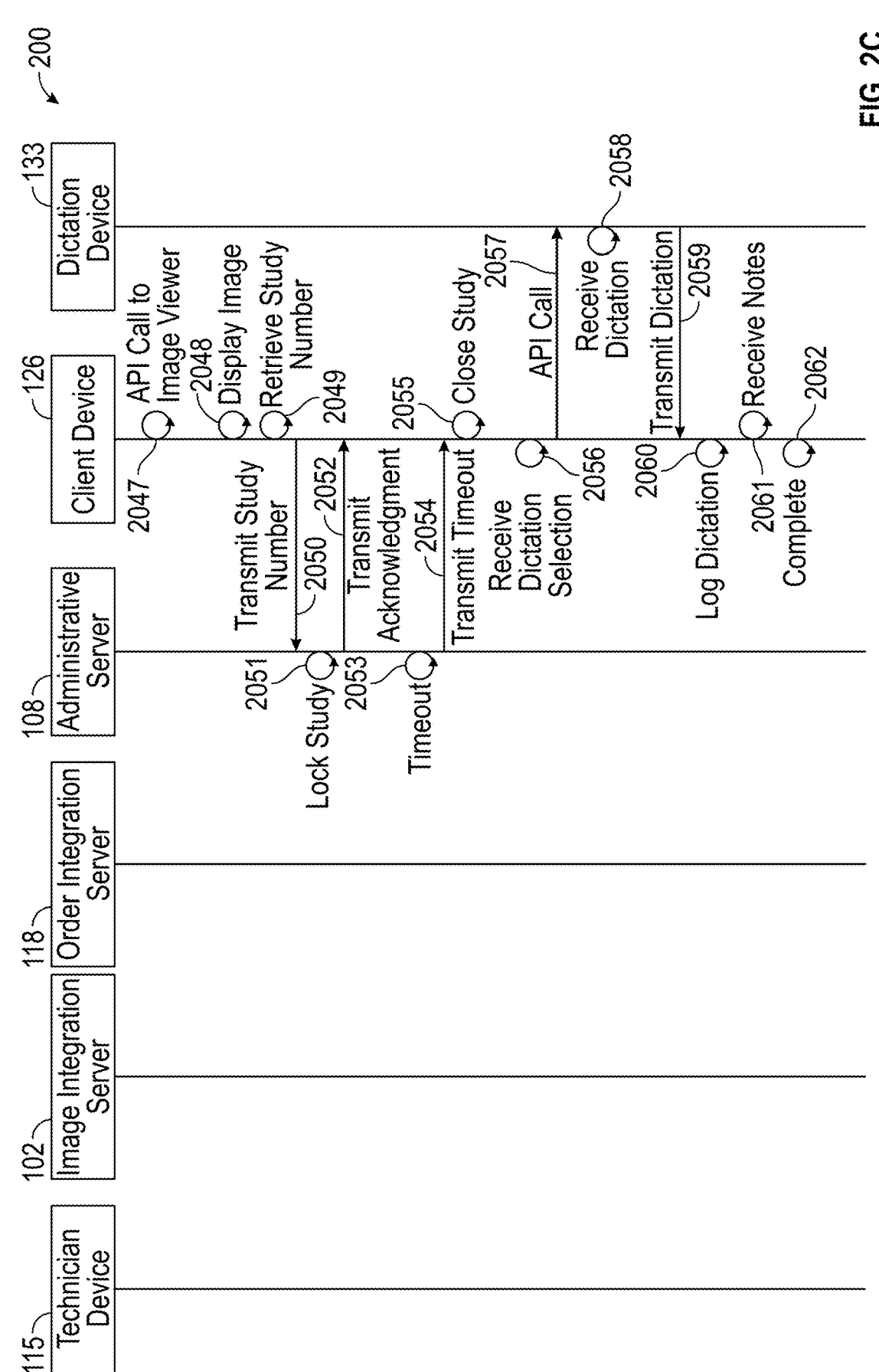
Figure 2D:
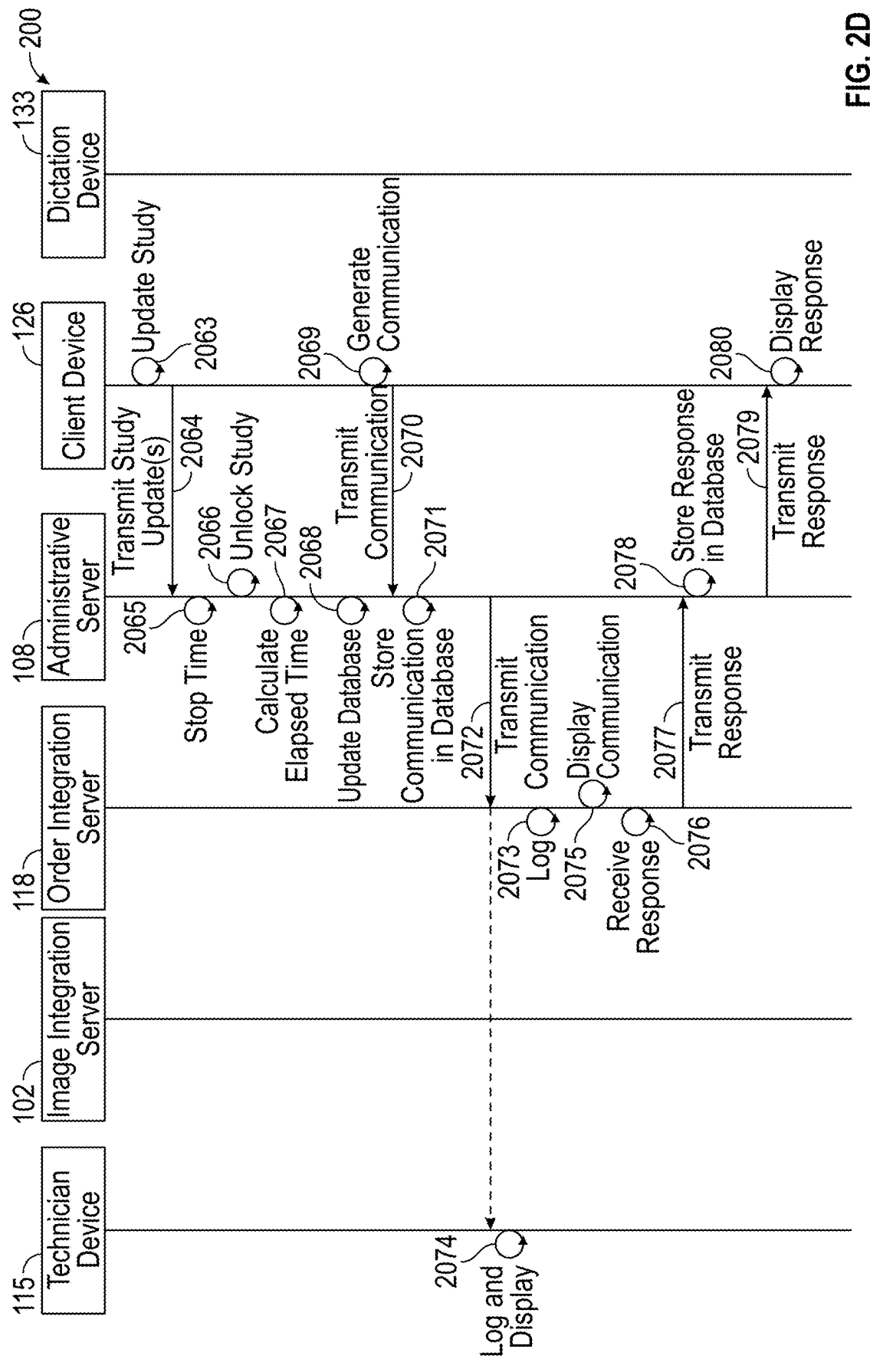
Figure 2E:
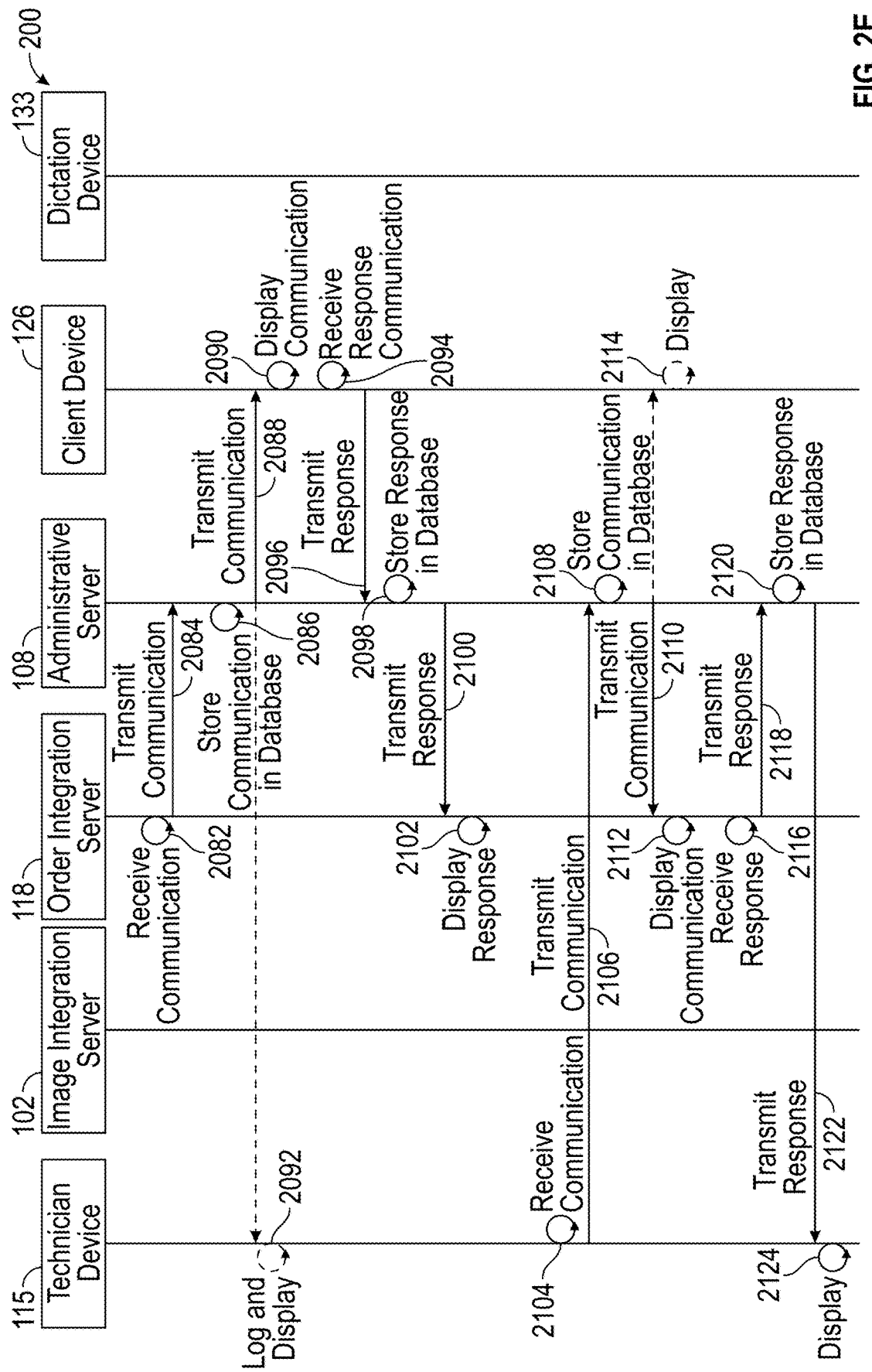

Referring then to FIG. 2A, at step 2002, order integration server 118 receives patient data, such as demographics, medical history, injury notes, and physiology of interest and a radiology order. At step 2004, the order integration server receives an image capture request including the number and position of images requested and modality.

At step 2006, the order integration server receives a priority indication, such as "stat", "urgent", or "routine". At step 2008, the order integration server generates a radiology order under a unique radiology order number, including the radiology order, the patient data, image capture request, and priority.

At step 2010, the order is transmitted to administrative server 108 and recorded in database 106. At step 2012, the administrative server generates a study file, containing the order and stores the study in the database, associated with the radiology order number.

At step 2013, the study is transmitted to technician device 115. At step 2014, the technician device unpacks the image capture request. At step 2016, technician device 115 receives the requested images. At step 2018, the images are then transmitted to image integration server 102.

At step 2020, the image integration server associates the images with the order according to the appropriate radiology order number. At step 2022, the images are transmitted to administrative server 108. At step 2024, the images are appended to the study and stored in the database.

At step 2026, the administrative server continuously queries the database for new images which have been marked "study requested". In a preferred embodiment, a query is submitted approximately every 10 seconds, so as to not over-tax the network. At step 2028 when a study request marking is detected, the administrative server retrieves the study containing the new images.

At step 2029, an elapsed time clock is started and associated with the study. The time clock runs until the study is completed, and an elapsed time field is associated with the study in the database. At step 2030, the priority of the study is determined, as will be further described. The priority of each study is then associated with the appropriate study based on the unique radiology order number.

At step 2031, optionally, the study is assigned to a radiologist based on various factors, such as location, study priority, radiologist specialty, radiologist credentialling, radiologist shift, and radiologist workload, as will be further described.

At step 2032, administrative server 108 updates the list of studies stored in the database with the radiologist assigned.

At step 2033, the administrative server queries the study list for "time violations." In a preferred embodiment, a time violation occurs when a study's elapsed time clock reaches a predetermined value without being completed. Predetermined values are set depending on the urgency of the study. In a preferred embodiment, "stat" priority is 1 hour, "urgent" priority is 6 hours, and "routine" priority is 24 hours.

At step 2034, if a time violation occurs, then the study priority is incrementally raised. In one embodiment, if a time violation occurs on a study with a stat priority, then an alert is generated and sent to the assigned radiologist and ordering physician. In another embodiment, if a time violation occurs on a study with a stat priority, then the study is reassigned to another available radiologist.

At step 2035, client device 126, usually associated with a radiologist, receives a request for an updated study list. In a preferred embodiment, the study list is a flat file identifying studies by the unique radiology order number. At step 2036, the request is transmitted to administrative server 108. At step 2037, the updated study list is retrieved from the database. At step 2038, the updated study list is returned to the client device. At step 2039, the updated study list is displayed on client device 126.

At step 2040, the study list is filtered at client device 126 to produce a study selection. In a preferred embodiment, the study list may be filtered by categories of priority, time in queue, patient name, location, patient medical record number (MRN) or study, status, patient age, or modality. Categories not elected are not displayed in the study list.

At step 2041, the client device receives a study selection. At step 2042, client device 126 periodically queries the administrative server to refresh the filtered study list. In a preferred embodiment, refresh queries are generated about every 10 minutes, but the refresh query rate may, of course, vary. At step 2043, the study selection is transmitted to administrative server 108. At step 2044, the selected study and associated images are retrieved from the database. Studies and images that have been "locked", as will be further described, are not retrieved from the database. Limiting retrieval to unlocked studies and images prevents duplication of effort and conflicting radiology reports and increases system efficiency by preventing generation of reports for studies that are currently under review. Limiting retrieval to unlocked studies also increases computational efficiency by eliminating transmission of unused data through the network. At step 2045, the study and images that are not locked are returned to the client device. At step 2046, the selected study details are displayed at the client device.

At step 2047, the client device sends an API call to the PACS software to display an image associated with a selected study. In another preferred embodiment, the client device issues an API call to a third-party image viewer, resident on the client device. At step 2048, the image is displayed on the client device. At step 2049, the client device retrieves the radiology number from the study. At step 2050, the study number associated with the image being viewed is transmitted to the administrative server. At step 2051, the administrative server marks each of the studies identified as "locked". Simultaneously, the administrative server starts a pendency clock on each locked file. At step 2052, a "locked" acknowledgement is transmitted to the client device. At step 2053, if the pendency clock on any locked file reaches a predetermined "timeout" limit, the file lock is removed, and the study is released for viewing by others. At step 2054, a timeout message is sent to the client device. At step 2055, the client device automatically closes the study.

At step 2056, the client device receives a dictation selection. At step 2057, an API call for dictation software 132 is transmitted to activate dictation device 133. At step 2058, dictation device 133 receives the dictation and creates a dictation file using the dictation software.

At step 2059, the dictation file is transmitted to client device 126. At step 2060, the dictation file is logged. At step 2061, the client device receives notes. In a preferred embodiment, the notes are stored in an ASCII text file. At step 2062, the client device receives a study "complete" selection, indicating that the report is completed.

At step 2063, the client device receives a selection to update, or save, the dictation and notes added to the study. In one embodiment, a selection of "complete" automatically saves the dictation file and notes. In another embodiment, the dictation is transcribed and the transcription is automatically saved upon completion.

At step 2064, the status, dictation, and notes are transmitted to administrative server 108. At step 2065, the elapsed time clock on the study is stopped when the status is changed to "complete". Likewise, the pendency clock is stopped. The values of the elapsed time clock and the pendency clock are both stored in the database associated with the study. At step 2066, the study is unlocked. At step 2067, the elapsed time between when the study was ordered and when the study was completed is calculated. At step 2068, the database is updated with the status, dictation, notes and elapsed time.

At step 2069, client device 126 generates a communication, such as a test request for reimaging or to add additional background on the results of a study. At step 2070, the communication is transmitted to administrative server 108. At step 2071, the communication is stored in the database, appended to the appropriate study.

At step 2072, the communication is transmitted to order integration server 118, and, if applicable, to technician device 115. At step 2073, the order integration server logs the communication. At step 2074, the technician device logs and displays the communication. At step 2075, the communication is displayed. In one preferred embodiment, the communication is sent from the order integration server to a physician device (not shown). At step 2076, order integration server 118 receives a response to the communication. At step 2077, the response is transmitted to administrative server 108. At step 2078, the response received is stored in the database, and associated with the appropriate study. At step 2079, the response is transmitted to client device 126. At step 2080, the response is displayed at client device 126.

At step 2082, communication is received at order integration server 118. At step 2084, the communication is transmitted to administrative server 108. At step 2086, the communication is stored in the database. At step 2088, the communication is transmitted to client device 126, and, if applicable, to technician device 115. At step 2090, the communication is displayed at client device. At step 2092, the technician device logs and displays the communication.

At step 2094, a response communication is received at client device 126. Optionally, a response communication may be received at the technician device. At step 2096, the response communication is transmitted to administrative server 108. At step 2098, the response communication is stored in the database, as previously described. At step 2100, the response is transmitted to order integration server 118. At step 2102, the response communication is displayed.

At step 2104, communication is received at technician device 115. At step 2106, the communication is transmitted to administrative server 108. At step 2108, the communication is stored in the database. At step 2110, the communication is transmitted to order integration server 118, and, if applicable, to client device 126. At step 2112, the communication is displayed. At step 2114, the client device displays the communication.

At step 2116, a response communication is received at order integration server 118. Optionally, a response communication may be received at the client device. At step 2118, the response communication is transmitted to administrative server 108. At step 2120, the response communication is stored in the database, as previously described. At step 2122, the response is transmitted to technician device 115. At step 2124, the response communication is displayed.

Figure 2F:
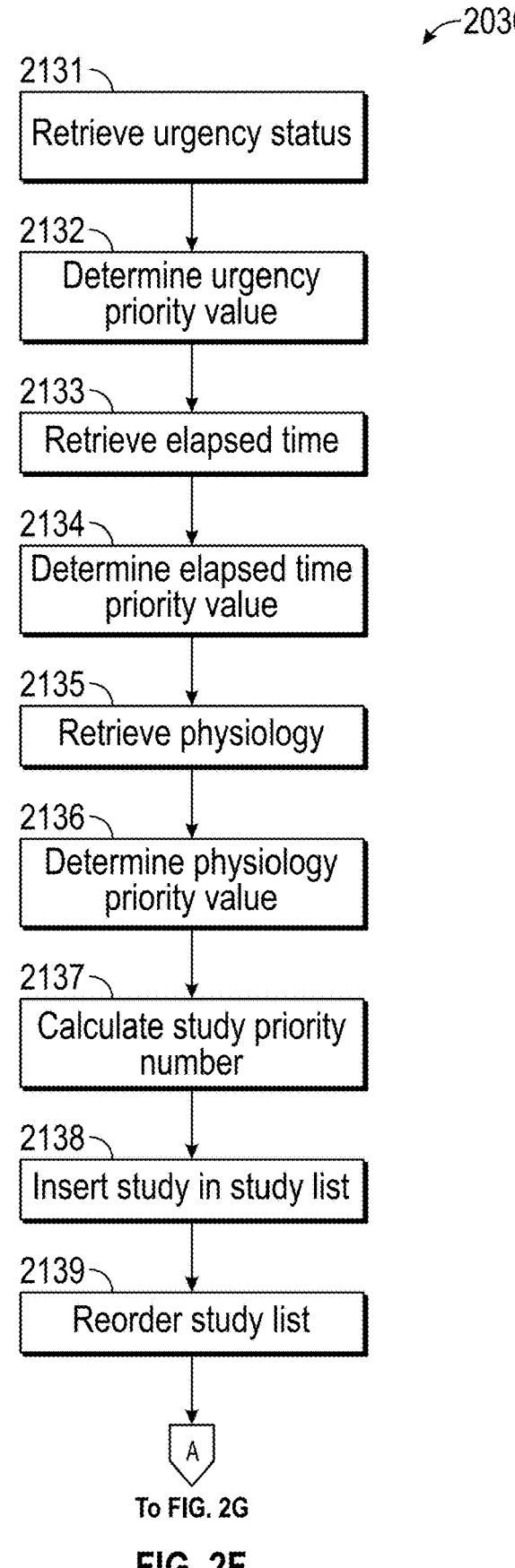
FIGS. 2F and 2G are a flowchart for a preferred method of study prioritization.
Figure 2G:
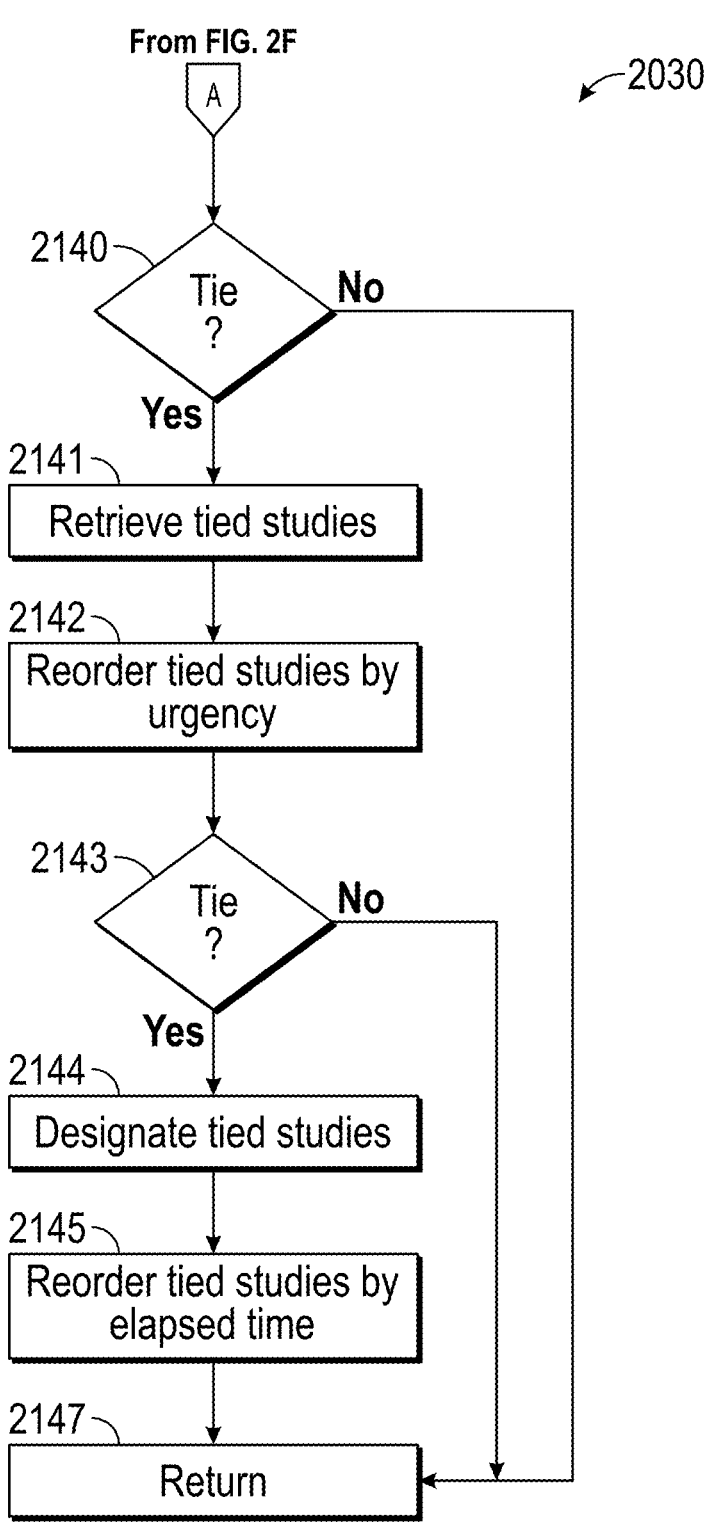

Referring then to FIGS. 2F and 2G, step 2030 for determining study priority in a preferred embodiment will be further described.

At step 2131, the system retrieves the urgency status of the current study, such as, "stat", "urgent", or "routine". At step 2132, the system determines the urgency priority value (UPV) of the study. In a preferred embodiment, the urgency value of a study is determined according to Table 1 below.

TABLE 1

| Urgency Status | Urgency Priority Value |
| --- | --- |
| Stat | 3 |
| Urgent | 2 |
| Routine | 1 |

At step 2133, the elapsed time, t, is retrieved. At step 2134, the elapsed time priority value, ETPV, is determined according to the following formula:

$$ETPV = \frac{t - (t \bmod 5)}{5}$$

Where:
t=is the elapsed time.

In a preferred embodiment, the modulus is 5. However, other modulus numbers may be used.

At step 2135, the system retrieves the study physiology designation. At step 2136, the physiology priority value (PPV) is determined. In a preferred embodiment, PPV may be determined according to Table 2 below.

TABLE 2

| Physiology Designation | Physiology Priority Value |
| --- | --- |
| Head | 10 |
| Chest | 9 |
| Neck | 8 |
| Spine | 7 |
| Abdomen | 6 |
| Pelvis | 5 |
| Humerus/Femur | 4 |
| Tibia/Fibula/Ulna/Radius | 3 |
| Joints | 2 |
| Phalanges | 1 |

At step 2137, the study priority number, SPN is calculated according to the following equation:

$$SPN = UPV + ETPV + PPV$$

Where:

SPN is the study priority number of the current study;

UPV is the urgency priority value of the current study;

ETPV is the elapsed time priority value of the current study; and,

PPV is the physiology priority value of the current study.

At step 2138, the current study is inserted into the study list. At step 2139, the study list is arranged in descending order, based on the SPN of each of the studies. At step 2140, the system queries whether or not one or more studies have the same SPN. If not, the method proceeds to step 2147 and returns. If so, then the method proceeds to step 2141.

At step 2141, all studies containing the same SPN are designated "tied studies" and removed from the study list. At step 2142, the tied studies are reordered by the UPV and reinserted into the study list. At step 2143, the system again queries whether or not a tie still exists. If no tied studies exist, then the method proceeds to step 2147. If so, then the method proceeds to step 2144.

At step 2144, the tied studies are designated and removed from the study list. At step 2145, the tied studies are reordered in descending order by the elapsed time value and reinserted in the study list. At step 2147, the studies are returned in their new order to the study list.

Figure 2H:
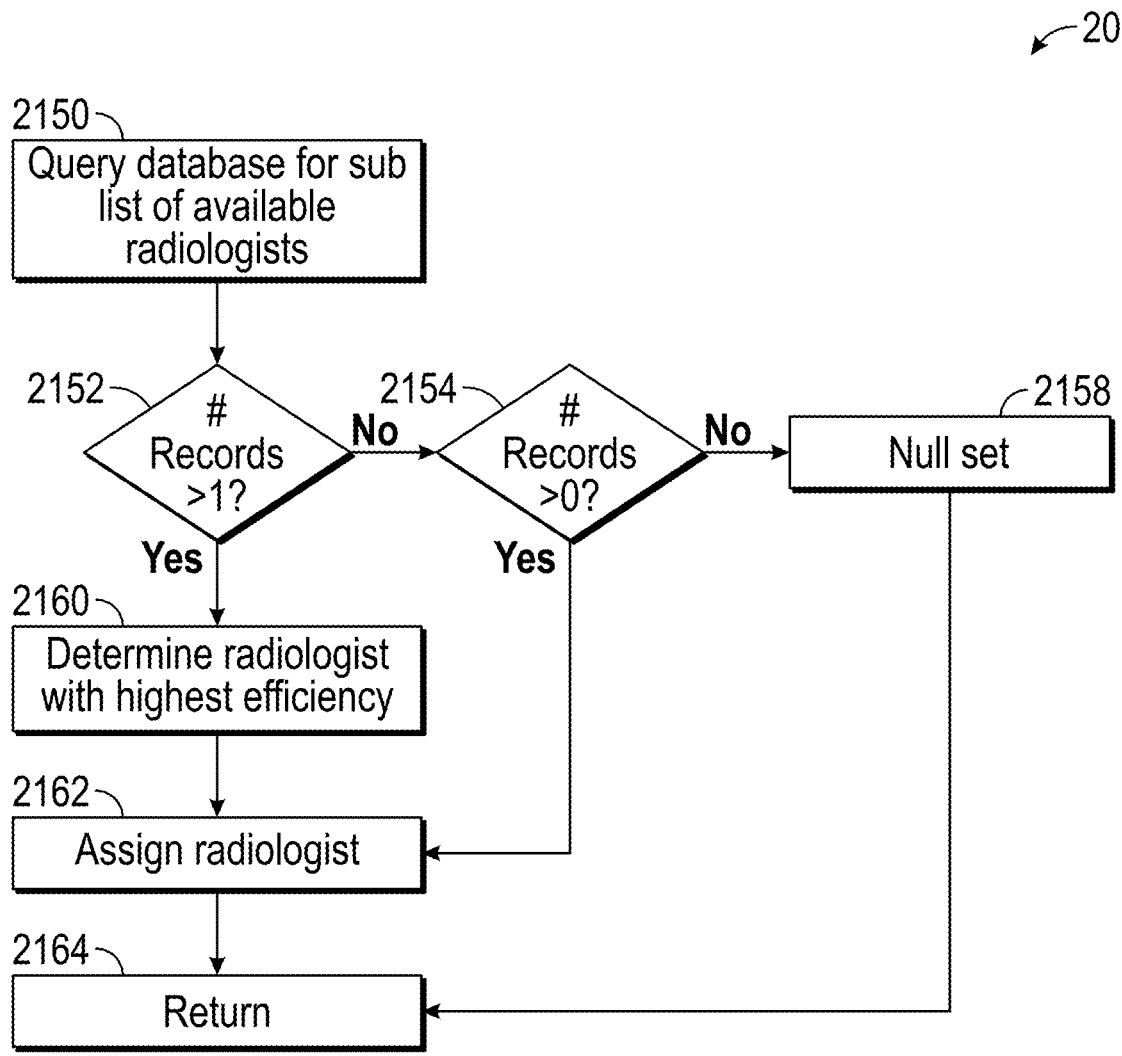
FIG. 2H is a flowchart for a preferred method of study assignment.

Referring then to FIG. 2H, step 2031 for optionally assigning a study to a radiologist in a preferred embodiment will be further described. In a preferred embodiment, the option to invoke step 2031 is made by the administrative server at system startup.

At step 2150, the system queries for a sub list of available radiologists. In a preferred embodiment, the system queries radiologist records for those that specifically align with the unassigned study details and a sub list is created, as will be further described.

At step 2152, the system determines whether or not the sub list of available radiologists contains more than one (1) record. If not, the method proceeds to step 2154. If so, the method proceeds to step 2160.

At step 2154, the system determines whether or not the sub list of available radiologists contains more than zero (0) records. If so, then the method proceeds to step 2162. If not, the method proceeds to step 2158. At step 2158, a null set occurs because no available radiologists can be assigned and the method proceeds to step 2164 and returns.

At step 2160, the system determines the available radiologist with the highest efficiency rating. At step 2162, a radiologist is assigned to the study. At step 2164, the updated study record is returned.

Figure 2I:
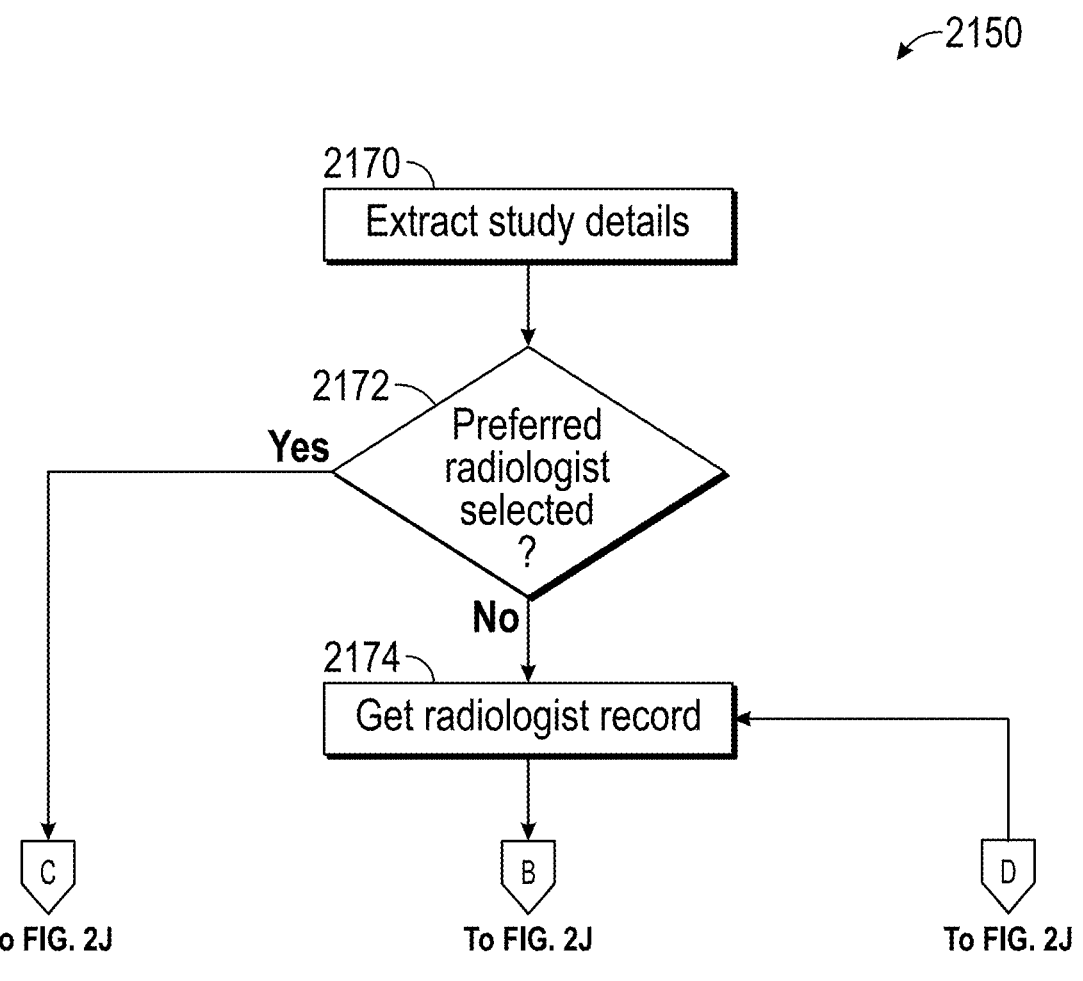
FIGS. 2I and 2J is a flowchart for a preferred method of querying a database for available radiologists.
Figure 2J:
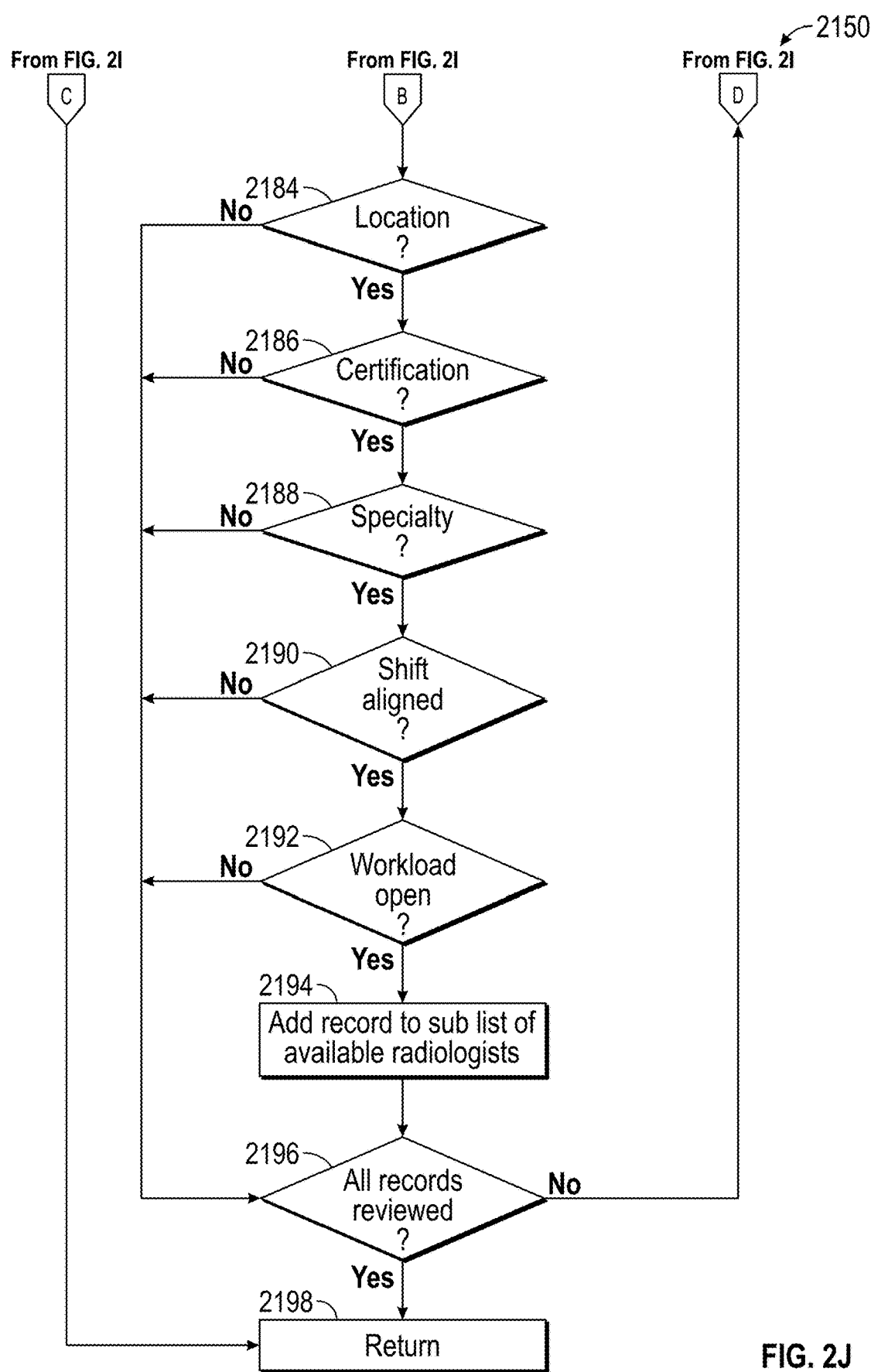

Referring then to FIGS. 2I and 2J, step 2150 for querying the database for available radiologists will be further described.

At step 2170, study details are extracted, from the database record such as the location, image type, injury physiology, urgency, preferred radiologist, and elapsed time.

At step 2172, the system determines whether or not the study record has a preferred radiologist selection. If so, the method proceeds to step 2198 and the preferred radiologist record is returned. If not, the method proceeds to step 2174.

At step 2174, a radiologist record is retrieved from the database.

At step 2184, the system queries if the location in the radiologist record matches the study location. In a preferred embodiment, the location for consideration for automatic assignment may optionally be expanded to include multiple locations in a hospital network. If so, then the method proceeds to step 2186. If not, then the method proceeds to step 2196.

At step 2186, the system queries if the radiologist record lists the required certifications to review the type of image associated with the study record. If not, then the method proceeds to step 2196. If so, then the method proceeds to step 2188.

At step 2188, the system queries if the radiologist record lists the specialty associated with the study physiology, such as pediatric or neurological. If not, the method proceeds to step 2196. If so, then the method proceeds to step 2190.

At step 2190, the system queries if the radiologist shift aligns with the study urgency and elapsed time. An alignment occurs when the radiologist is on duty with enough shift time to review the study without causing a time violation. If not, the method proceeds to step 2196. If so, the method proceeds to step 2192.

At step 2192, the system queries if the radiologist workload is open. In a preferred embodiment, a radiologist workload is restricted to a predetermined number, such as two (2), assigned studies per hour, or a total of ten (10) assigned studies per shift. Once the predetermined number of assigned studies is reached, the radiologist workload is considered closed. Different numbers of assigned studies and additional restrictions may be utilized, such as the number of "stat" or "urgent" studies assigned. If not, the method proceeds to step 2196. If so, then the method proceeds to step 2194 and adds the radiologist record to a sub list of available radiologists.

At step 2196, the system determines whether or not all records have been reviewed. If not, the method returns to step 2174 and retrieves the next record. If so, then the sub list of all available radiologists is returned at step 2198.

Figure 3A:
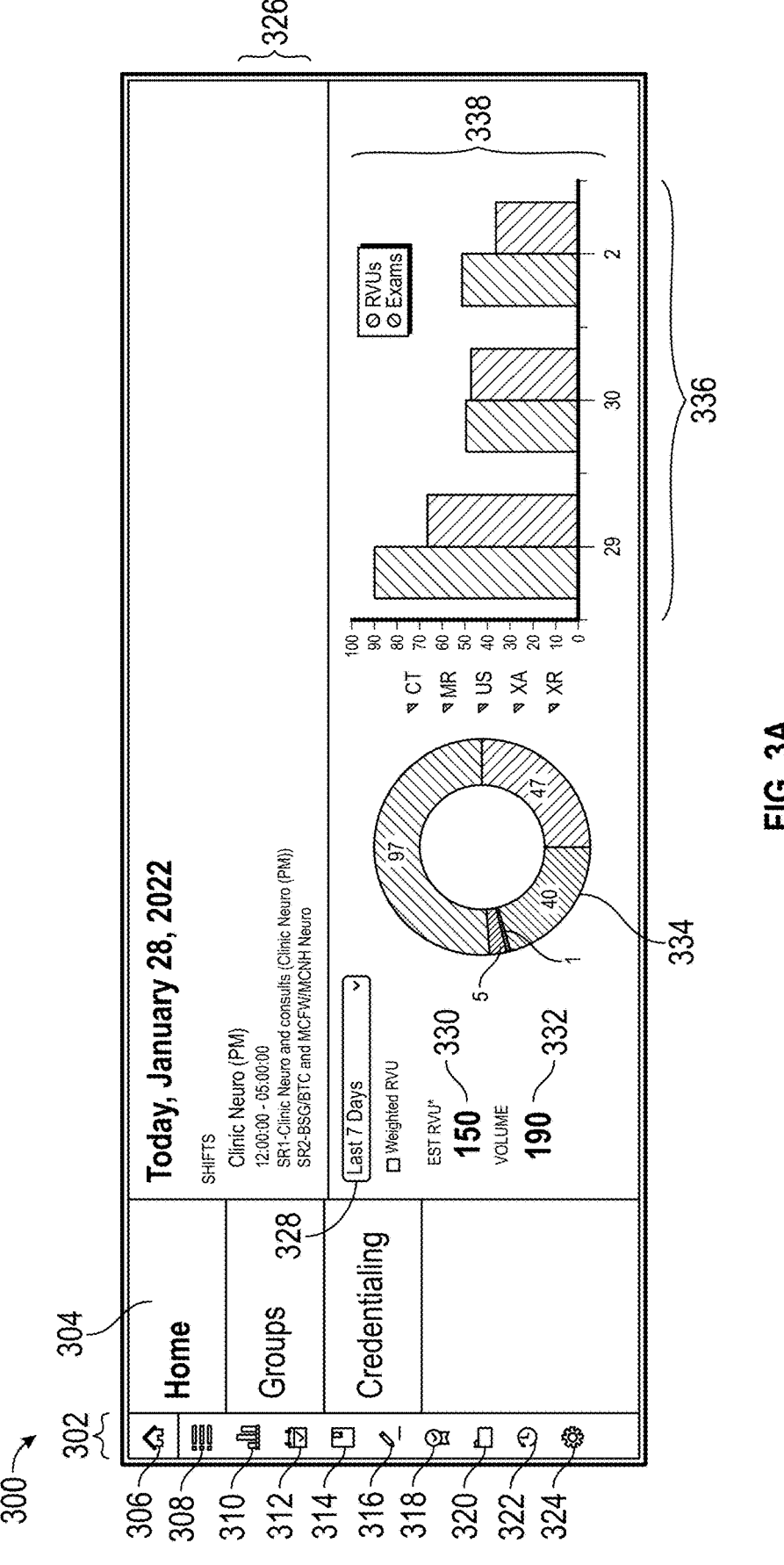
FIG. 3A is a screenshot of a graphic user interface for a home screen of a preferred embodiment.

Referring then to FIG. 3A, home screen 300 will be described.

Home screen 300 includes menu column 302. Menu column 302 includes home button 306 and home tab 304. When home button 306 is selected the system returns to home screen 300. Menu column 302 also includes worklist button 308. When worklist button 308 is selected, the system displays the user's worklist, which will be further described. Analytics button 310 is also located in menu column 302. When analytics button 310 is selected, the system displays to the user's progress and productivity metrics, which includes, but is not limited to, the number of exams reviewed by shift for the time and date selected, as will be further described. Menu column 302 also includes calendar button 312, resources button 314, notes button 316 and credential button 318. When calendar button 312 is selected, the system displays to the user's calendar. When resources button 314 is selected the system displays a list of medical facilities that includes the website link for each facility. When notes button 316 is selected, the system displays the user's saved notes. When credential button 318 is selected, the system displays the user's credentials.

Menu column 302 also includes folders button 320. When folders button 320 is selected, the system displays a list of saved folders. History button 322 is also found under menu column 302. When history button 322 is selected, the system displays a list of studies that have been read for a particular time period selected. Menu column 302 further includes settings button 324. When settings button 324 is selected, the system displays settings dialog box where the user can modify personal settings, such as shift and open orders on dictation, profile settings, site credentials settings, and VPN credentials settings.

Home screen 300 lists current shift 326 and performance data 338 for a specified time period. Home screen 300 includes time period drop down menu 328 that allows the user to select different time periods, such as 7 days and 30 days. When time period drop down menu 328 is selected, the metrics on home screen 300 are refreshed to show updated information for the selected period of time. Estimated RVU 330 is a measure of productivity and is shown for the time period and shift selected and updates when time period drop down menu 328 is updated to a new time period. Studies reviewed 332 shows the number of studies the user has reviewed for the time period and shift selected. Studies reviewed 332 also updates when time period drop down menu 328 is updated. The studies the user reviews for a specified time period are shown in pie chart 334. Pie chart 334 details the studies reviewed by modality. Bar graph 336 displays RVU 330 and studies reviewed 332 by days in the radiologist shift identified in current shift 326.

Figure 3B:
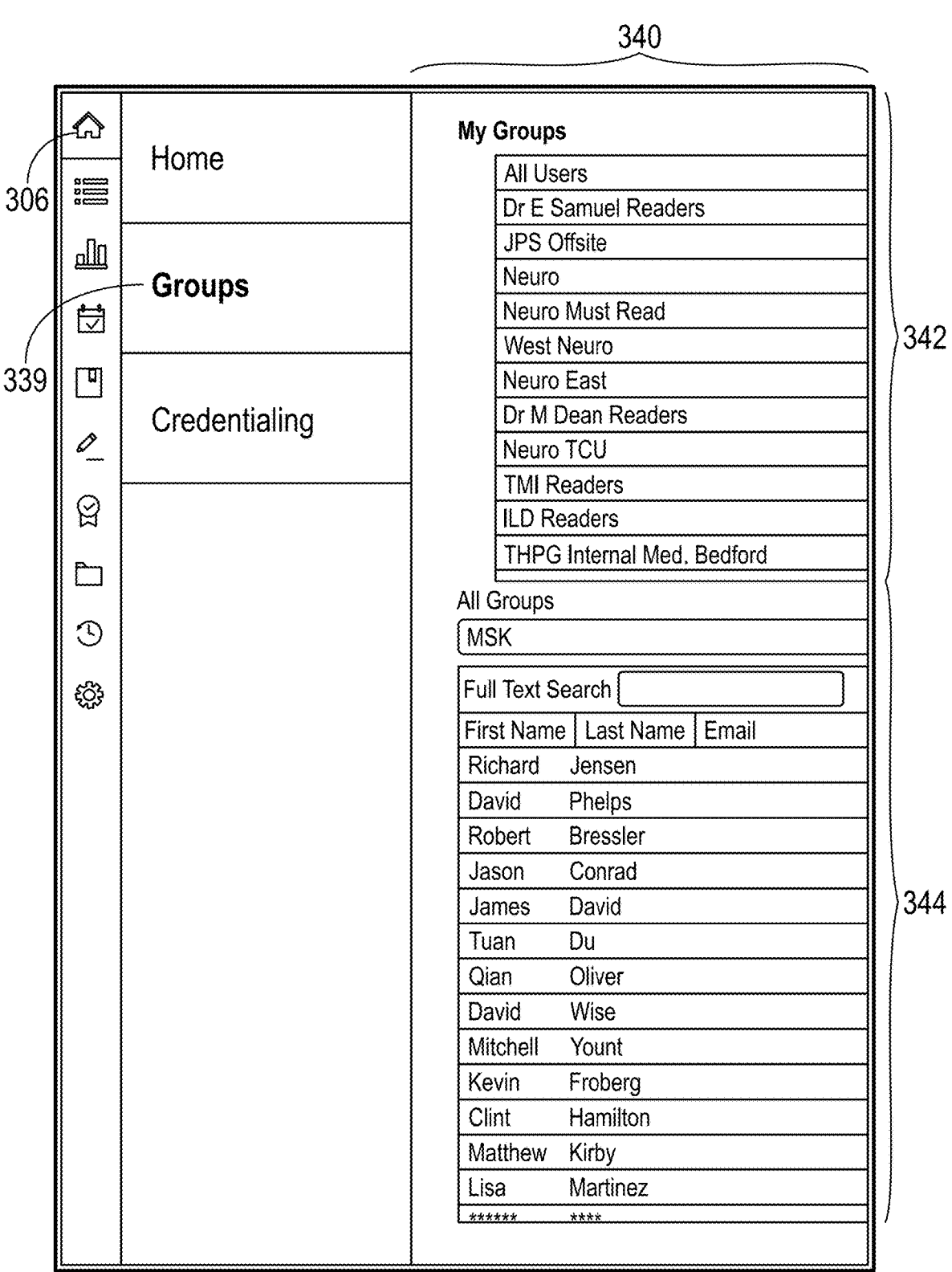
FIG. 3B is a screenshot of a graphic user interface for a groups tab selection of a preferred embodiment.

Referring then to FIG. 3B, home button 306 includes groups tab 339. When groups tab 339 is selected, my groups list 342 and all groups list 344 are shown under groups column 340. My groups list 342 are all the groups of which the user is a member. All groups list 344 is a list of all currently available groups. The user can select a group from all groups list 344 to see all current members of the selected group.

Referring then to FIG. 3C, home button 306 includes credentialing tab 346. When credentialing tab 346 is selected, my credentials list 350 and credentials by site list 352 are shown under my credentials column 348. My credentials list 350 lists all the credentials for the user. Credentials by site list 352 is a list of all credentials by site and the user can select a particular site to see how other users are credentialed.

Figure 4A:
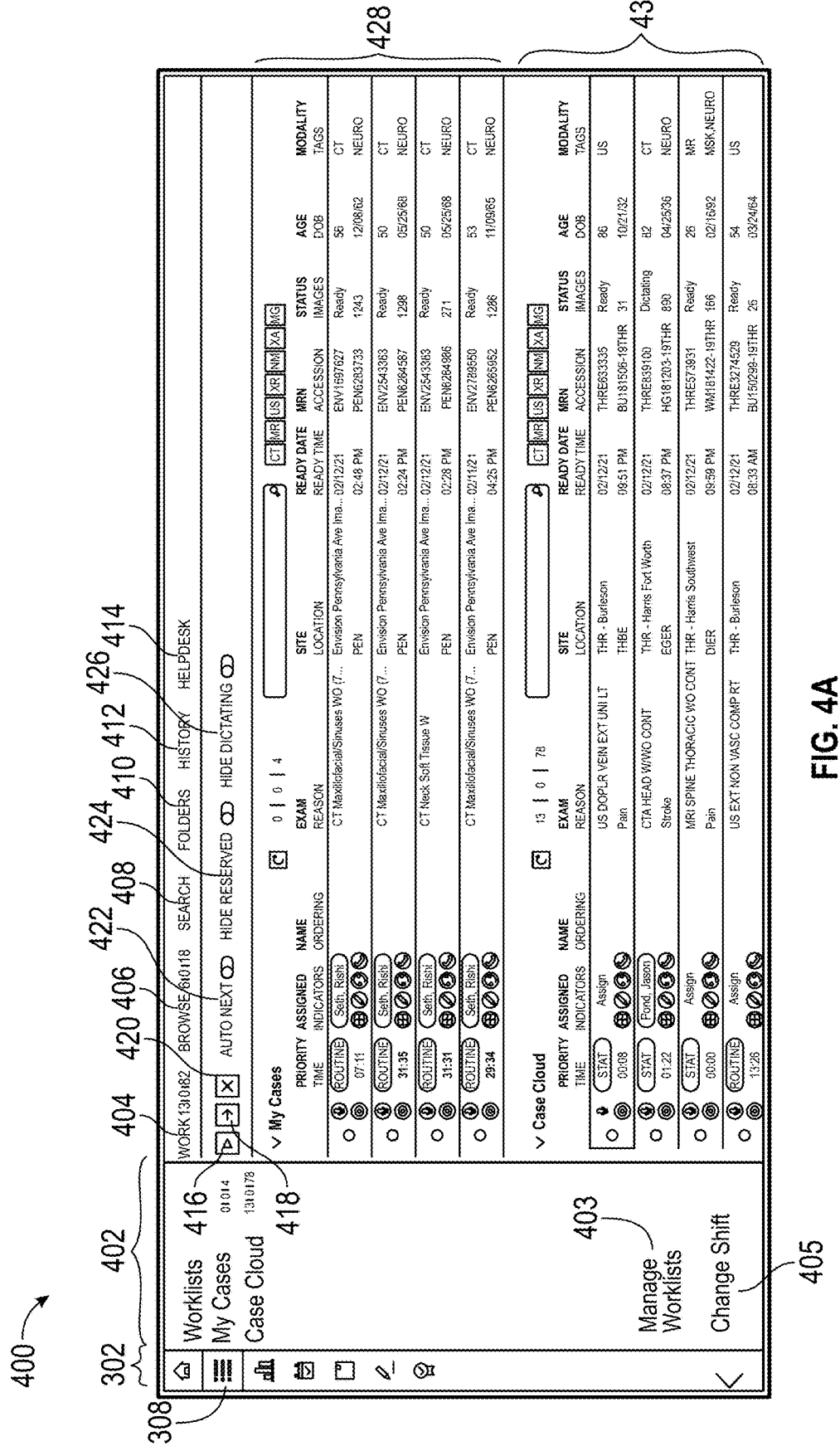
FIG. 4A is a screenshot of a graphic user interface for a worklist summary tab selection of a preferred embodiment.
Figure 4B:
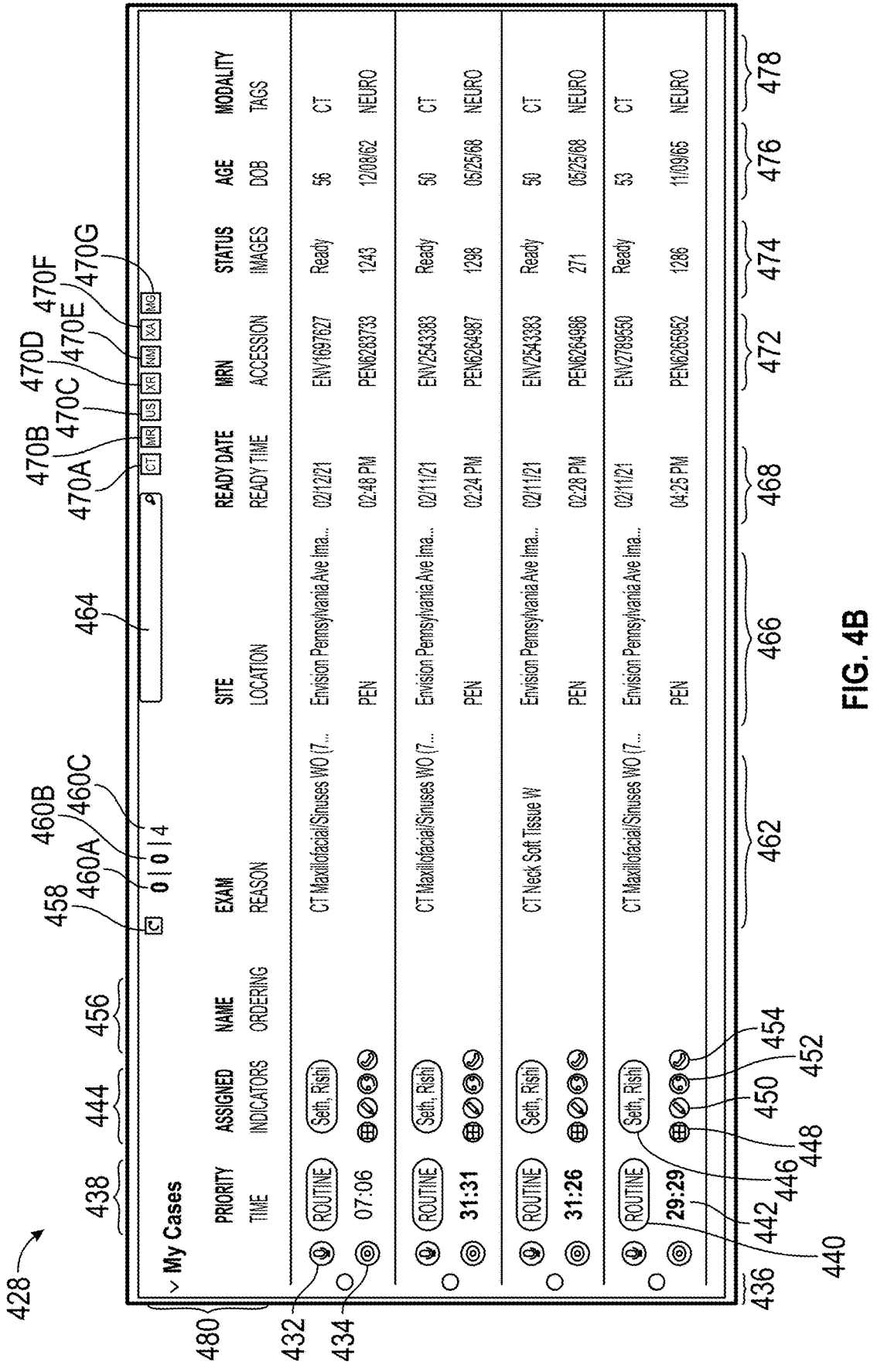
FIG. 4B is a screenshot of a graphic user interface for a worklist summary tab selection of a preferred embodiment.

Referring then to FIGS. 4A and 4B, a preferred embodiment of a graphic user interface worklist summary 400 will be further described.

Worklist summary 400 includes a list of outstanding review requests assigned to the user. The worklist includes menu column 302 and worklist button 308. When worklist button 308 is selected, the system displays worklist summary 400. Worklist summary 400 includes worklist column 402. Worklist column 402 displays "My Cases" 428 and "Case Cloud" 430. My Cases 428 includes studies assigned to the user through automatic assignment or self-assignment. Case Cloud 430 includes all studies that are currently unreviewed but are available for review by the user based on the users profile and credentials.

Worklist summary 400 also includes work button 404, browse button 406, search button 408, folders button 410, history button 412, and helpdesk button 414. When work button 404 is selected, the system displays My Cases 428 and Case Cloud 430. Work button 404 shows the number of studies that are in stat, urgent, and routine status.

When browse button 406 is selected, the system displays the users currently assigned studies. The users actively saved worklists, favorites, and groups are displayed under browse button 406. The saved worklists, favorites, and group lists may be organized based on discipline, clinics, hospitals, or work groups. The groups may be viewed together or individually.

When search button 408 is selected, the system displays a screen that includes a quick search option and an advanced search option.

When folders button 410 is selected, the system displays the folders screen which allows creation and manipulation of patient file folders.

When history button 412 is selected, the system displays a screen showing all studies read by a radiologist for a time period selected.

When helpdesk button 414 is selected, the system displays a screen that allows the user to seek technical assistance with the workflow management system.

Worklist summary 400 further includes "play" button 416. When play button 416 is selected, the system opens dictation software for dictating a study. The user can select multiple studies. The studies selected will be executed in the order of selection so the studies can be reviewed and dictated. If a patient has more than one study available for review, a dialog box will appear asking the user to review the studies for that patient. The user can choose "Que Next", "Continue", or "Cancel". If the user chooses "Que Next", the additional unreviewed study will be added to the studies list in the dictation software system. If the user chooses "Ignore", the additional unreviewed study will not be added to the list of selected unreviewed cases.

Worklist summary 400 also includes skip button 418, clear selection button 420, auto next slider 422, hide reserved slider 424, and hide dictating slider 426. When skip button 418 is selected, a user can skip a study and move to the next study in the queue. A skipped study is removed from the worklist. When clear selection button 420 is selected, the studies previously selected will be deselected and the work queue cleared of any active filters. When auto next slider 422 is selected, a user can select play button 416 and studies will be reviewed and dictated from the top-down. When the user is finished reviewing and dictating the first study in the list, the second study will be automatically queued for review and dictation. When the second study is completed, the third study will be queued, and so on, until all studies are reviewed or until the user decides to exit the queue. When hide reserved slider 424 is selected, all studies that are assigned to a different user or assigned to a group of which a radiologist is not a member, will be hidden from view on the worklist. When hide dictating slider 426 is selected, all studies currently in active dictation status will be hidden from view. Hide dictating slider 426 allows the user to filter the worklist of studies that are currently being reviewed which saves time and prevents unnecessary scrolling of the worklist by a user to find cases that are currently unreviewed.

Manage worklists button 403 and shift selection button 405 are located in worklist column 402 on worklist summary 400. Shift selection button 405 allows a user access to a shift selection box, as will be further described. Manage worklists button 403 allows a user to access the worklist manager dialog box. The worklist manager dialog box allows a radiologist to search by site to create certain lists, such as main worklist, group 1, group 2, or favorites. A site is added to one of these lists by highlighting the site and selecting the add button. A site can also be removed from one these lists by highlighting the site and selecting the remove button. If a site is added under favorite, that site is permanently stored as a favorite site. If a site is added under main worklist, that site is only saved for the session for which the radiologist is logged in currently.

Referring to FIG. 4B, a detailed view of My Cases 428 will be further described. My Cases 428 includes dictate button 432, view button 434, and study selection button 436. When dictate button 432 is selected, third party dictation software is automatically launched so the user can generate a report for the selected study, as will be further described. When view button 434 is selected, any images attached to the patient's file will open in a separate window, as will be further described. In a preferred embodiment, study selection button 436 allows the user to select multiple studies to open and review. An additional option to open the dictation software and the image viewer is to right click on the patient's name and a dialog box will appear with the options to dictate exam and view images. This dialog box also includes "Add to Queue", which allows the user to add the study to the list of studies for dictation, "Skip/Un-skip Exam", and "View Exam Manager". Skip/Un-skip Exam allows the user to skip or un-skip a previously skipped study for review. If a study is skipped, it is removed from the user's worklist. View Exam Manager allows the user to easily access any notes attached to the patient file and any prior studies for the patient.

Worklist summary 400 includes study summaries header list 480. Study summaries header list 480 includes columns of priority, time, assignment, patient's name, ordering physician's name, exam, reason, site, location, ready date and time, medical records number, status, date of birth, and image modality. My Cases 428 includes priority and time column 438. Priority and time column 438 further includes status icon 440 and time elapsed icon 442. Status icon 440 provides the current priority status of each study, which can be "stat", "urgent", or "routine". In one preferred embodiment, status icon 440 is one color when studies are classified as stat, another color when studies are classified as urgent, and a different color when studies are classified as routine. Any number of color combinations may be used to differentiate the study priorities. Alternatively, a master study priority number for each study, calculated by the administrative server is displayed in the icon. Elapsed time icon 442 indicates the amount of time elapsed since a study has been available for review. In one preferred embodiment, elapsed time icon 442 will show in one color if 50% of service level agreement time has elapsed and, in another color, if 75% of service level agreement time has elapsed. In one preferred embodiment, when time elapsed icon 442 for each cases reaches the 50% threshold these studies will automatically be escalated in the worklist queue.

Worklist summary 400 also includes assigned and indicators column 444. Assigned and indicators column 444 further includes assign icon 446, review icon 448, study notes icon 450, telerad assistance icon 452, and call request icon 454. Assign icon 446 indicates the user that is assigned to review the study. If the study is assigned to the user, then assign icon 446 is highlighted one color and lists the users name. If the study is assigned to one of the user's groups, then assign icon 446 is highlighted in a different color and lists the group's name. If the study is not assigned, then assign icon 446 shows "Assign" highlighted in another color and gives the user or other individual the opportunity to assign the study to himself or to another for review. To assign a study to a user, the user can select assign icon 446 which is highlighted in a different color, or the user can select and choose "Assign to Me" from the dialog box. If a study is currently being dictated, then assign icon 446 is highlighted in yet a different color and other icons are inactive, but if a study is simply assigned to a different user and not being dictated, then assign icon 446 is inactive and all other icons are active. Assign icon 446 is highlighted in a different color when the user is actively dictating a study. In a preferred embodiment, any number of different color combinations may be used.

Review icon 448 indicates whether a study is ready for review. If a study is ready for review, then review icon 448 is highlighted one color, if a study is not ready for review, it is highlighted in a different color. Hovering over review icon 448, provides a list that includes the current status, the number of images, the number of documents, and if there is an existing report. Study notes icon 450 is highlighted one color if there are any notes in the patient file for that study, if not, study notes icon 450 is highlighted a different color. Hovering over this icon shows the number of notes in the patient file for that study. Telerad assistance icon 452, if activated, will be highlighted, and indicates whether communication with the referring physician, nurse, or technician has been requested by the user. Call request icon 454 will be highlighted if a user needs to return a request for a phone call from a physician, nurse, or technician. In a preferred embodiment, any number of different highlight color combinations may be used.

Worklist summary 400 also includes name and ordering column 456 and exam and reason column 462. Name and ordering column 456 includes the patient's name and ordering physician information. Exam and reason column 462 includes the type of exam the patient received, such as CT, MRI, or X-ray, and the medical reason for the exam, or the patient condition, the urgency rating and optionally the study priority number.

Refresh button 458 and worklist study numbers 460A, 460B and 460C are included in worklist summary 400. Refresh button 458 refreshes a user's worklist when selected. Worklist study number 460A represents the number of cases in a worklist that are "stat". Worklist study number 460B represents the number of cases in a worklist that are "urgent". Worklist study number 460C represents the number of cases in a worklist that are "routine".

Worklist summary 400 further includes search text box 464, site and location column 466, and ready date and ready time column 468. Search text box 464 allows a user to search and filter the worklist, including but not limited to, by patient name, site name, assigned radiologist, and current status. When a user searches by stat status, for example, the user's worklist will refresh and will list all cases that are currently classified as stat. All other studies that are not classified as stat will not be listed in the worklist. Site and location column 466 lists the information for the facility that performed the patient's exam. Ready date and ready time column 468 list the date and time a particular study became available for review.

Worklist summary 400 provides modality filters 470A, 470B, 470C, 470D, 470E, 470F and 470G. The modality filters organize worklist by modality. Modality filter 470A filters by CT studies. Modality filter 470B filters by MRI studies. Modality filter 470C filters by ultrasound studies. Modality filter 470D filters by X-ray studies. Modality filter 470E filters by nuclear medicine studies. Modality filter 470F filters by X-ray angiography studies. Modality filter 470G filters by mammogram studies. When one or more of the modality filters are selected, they are highlighted one color, and the selected studies will be listed in the worklist. When any of the modality filters are not selected, they are highlighted in another color and will not be listed in the worklist.

Worklist summary 400 also includes medical record number and accession column 472, status and images column 474, age and date of birth column 476, and modality and tags column 478. Medical record and accession column 472 are unique to each patient and each exam facility to uniquely identify each patient. Status and images column 474 indicates whether a study is ready for review and how many images are included in the study for review. Modality and tags column 478 indicates they type of exam received, such as CT or MRI, and the general area of the patient's body that was examined, such as neuro.

Figure 5A:
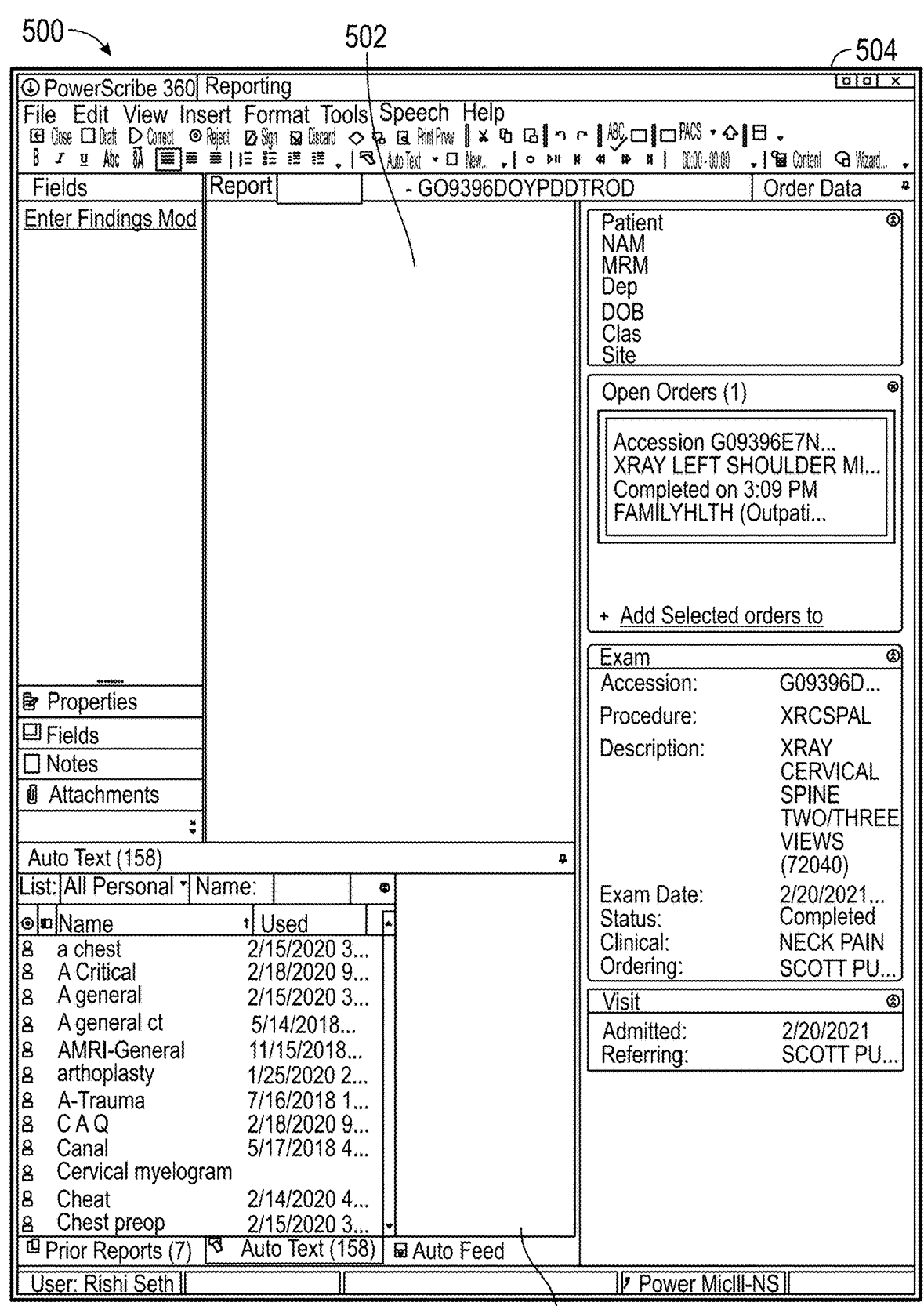
FIG. 5A is a screenshot of a graphic user interface for dictation application of a preferred embodiment.

Referring then to FIG. 5A, dictation software 500 will be further described.

Dictation software 500 includes GUI screen 504 and includes a patient's exam and allows a user to perform multiple actions and functions related to the exam report through the use of different icons and buttons, such as editing the text after dictation and includes reporting space 502, GUI screen 504, and signature block 506. In a preferred embodiment, the dictation software is PowerScribe 360, available from Nuance Communications of London, England. Dictation software 500 automatically launches when the user selects dictate button 432. Reporting space 502 is the space to dictate the study report that will be attached to the patient's file for physician review once the report is complete. Dictation software 500 also allows the user to make text notes that are attached to the patient's study. Signature block 506 allows a user to manually enter a signature for a completed report.

Figure 5B:
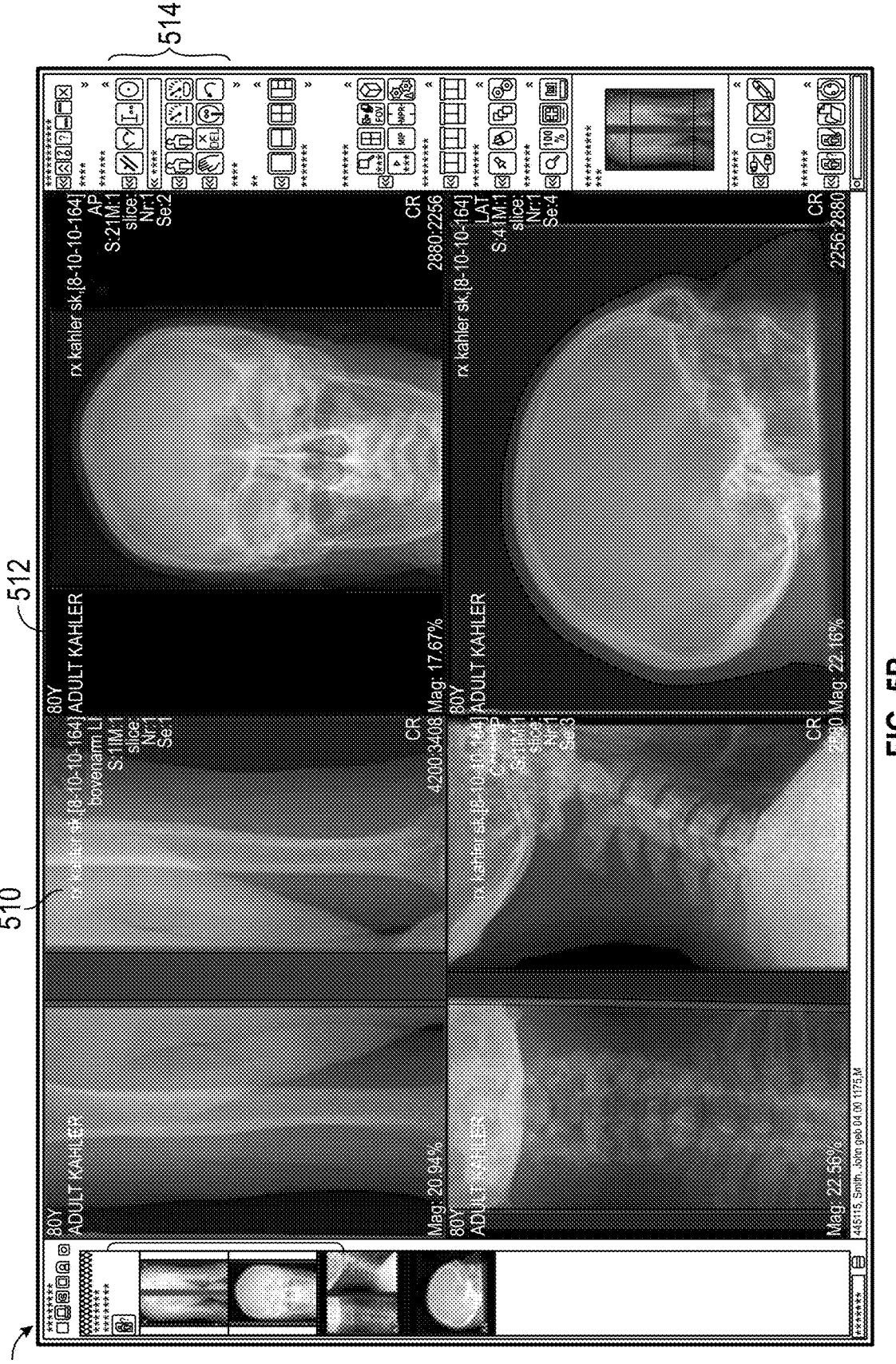
FIG. 5B is a screenshot of a PACS application of a preferred embodiment.

Referring then to FIG. 5B, imaging software system 508 will be further described.

Imaging software system 508 includes GUI 512. GUI 512 includes images display 510, and imaging icons 514. Imaging software system 508 provides the images of the patient to be reviewed and is launched when a user selects view button 434. GUI 512 provides imaging icons 514 to manipulate and adjust the view of the images. In a preferred embodiment, the imaging software is Synapse® PACS, available from Fujifilm Holdings America Corporation, located in Valhalla, New York.

Figure 6A:
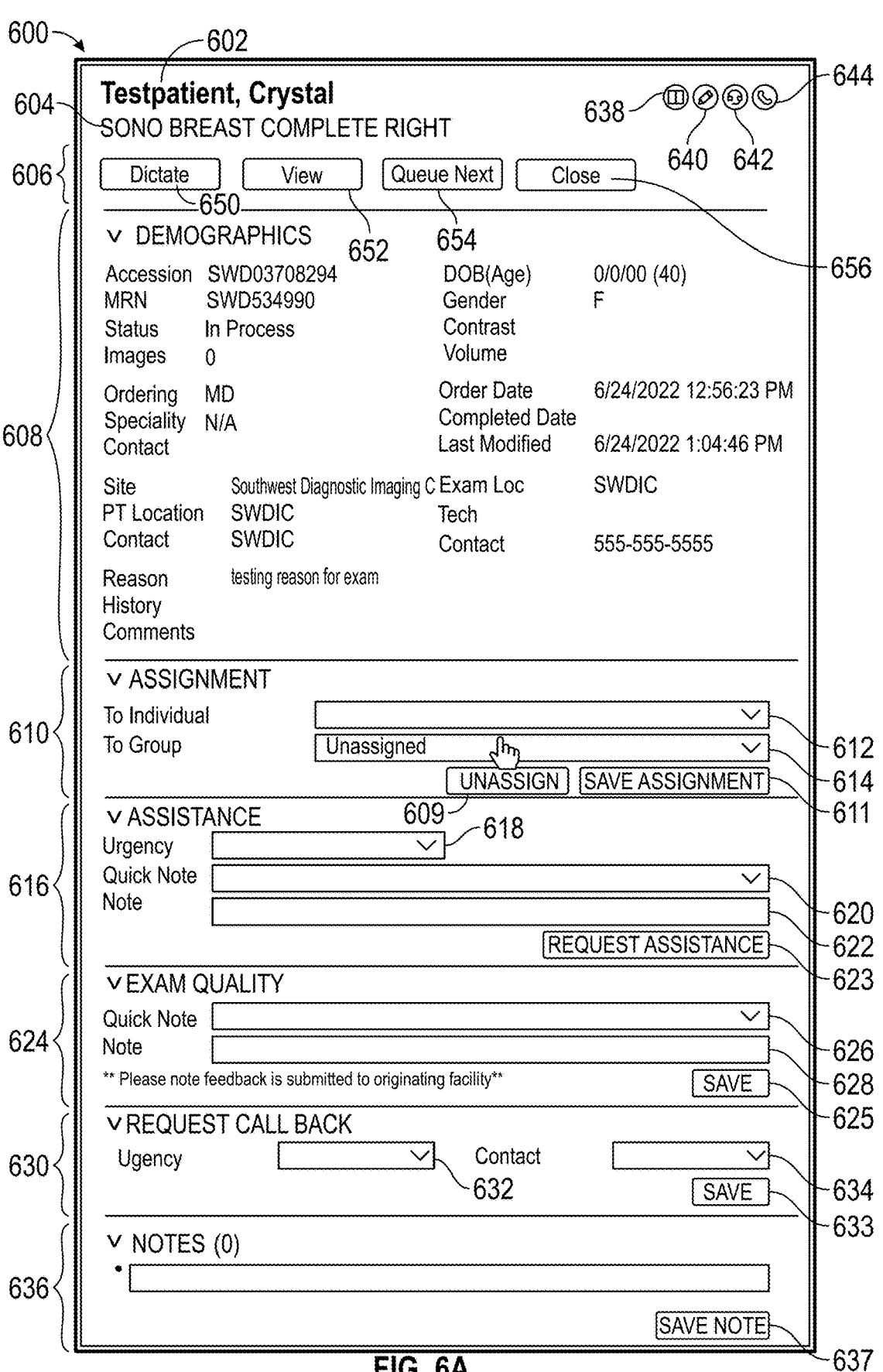
FIG. 6A is a screenshot of a graphic user interface of a patient profile of a preferred embodiment.
Figure 6C:
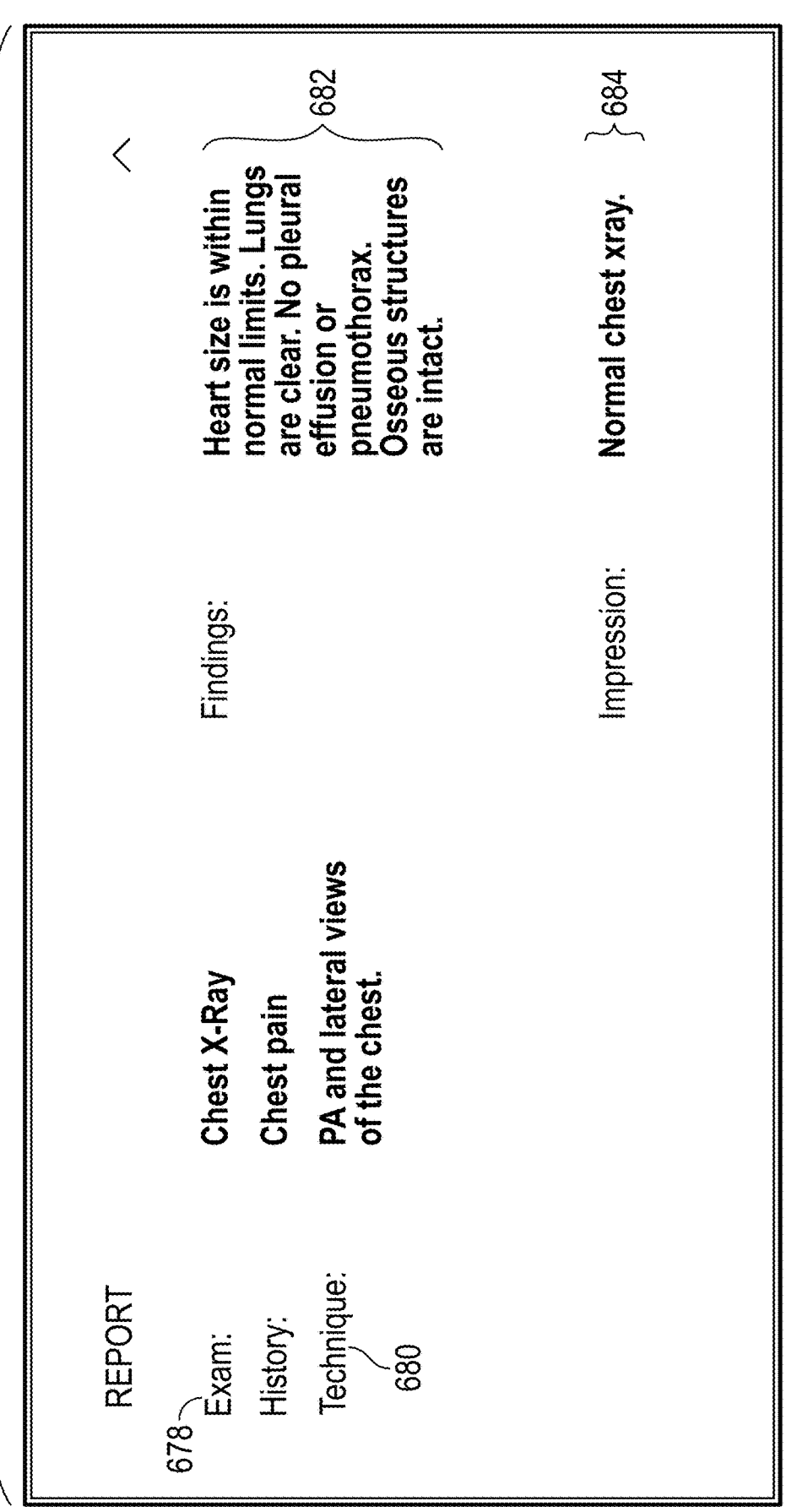

Referring then to FIGS. 6A, 6B, and 6C patient jacket 600 will be further described.

Patient jacket 600 includes patient name 602, exam received 604, and exam option buttons 606 for the selected patient. Patient jacket 600 is opened when a user selects assign icon 446 or right clicks the patient information and selects the view patient jacket option from the dialog box. Exam received 604 is the particular exam the patient received.

Exam option buttons 606 includes dictate button 650, view button 652, queue next button 654, and close button 656. When dictate button 650 is selected, the associated dictation software system will automatically launch so the user can dictate a report. When view button 652 is selected, the associated imaging software system will launch, and the radiologist will be able to review exam images. Queue next button 654 opens the current study and the patient jacket will automatically skip to the next study. The study that was skipped will be removed from the user's worklist. If a user selects close button 656, then the patient jacket is closed, and all changes are saved.

Patient jacket 600 also includes demographics section 608, assignment section 610, assistance section 616, exam quality section 624, request call back section 630, and notes section 636. Demographics section 608 displays patient information, such as gender, birthdate, ordering physician information, such physician name and order date, site where the exam was performed, exam modality, and how many images are attached, and the reason for the exam. Assignment section 610 includes individual drop down menu 612 and group drop down menu 614 to choose an individual or a group to assign the study. Assignment section 610 also allows a user to assign, unassign or reassign a study to a user.

To unassign a study, then an individual or group name is chosen from individual drop down menu 612 or group drop down menu 614 and unassign button 609 is selected. If a study is to be reassigned, then a new individual or group will be chosen from individual drop down menu 612 or group drop down menu 614 and save assignment button 611 will be selected. Once save assignment button 611 is selected and a study is assigned to a particular user, that study will appear on their worklist for review.

Assistance section 616 provides a user with the option to submit a request for assistance. Assistance section 616 includes urgency drop down menu 618, quick note drop down menu 620, and note text box 622. Urgency drop down menu 618 provides three options, namely, "high", "medium", and "low", but other options may be provided. In one embodiment, priority is assigned to the studies classified as having the highest urgency priority number if there are not other studies with the same urgency number. In another embodiment, the priority of the studies is assigned by elapsed time on the system. Quick note drop down menu 620 allows a user to choose from a predetermined list of messages. Note text box 622 allows a user to enter a text message from the keyboard. Once the assistance information is added to assistance section 616, request assistance button 623 is selected. When button 623 is selected, a message is sent to the referring physician, nurse, or technician.

Exam quality section 624 includes quick note drop down menu 626 and note text box 628. Exam quality section 624 allows a user to provide feedback on the quality of the exam and images in the patient file. Quick note drop down menu 626 includes a predetermined set of text messages which can include positive and negative feedback. Note text box 628 allows the user to enter a message from the keyboard. Once the information is added to exam quality section 624, save button 625 is selected and the information is saved to the patient file for that study.

Request call back section 630 includes urgency drop down menu 632 and contact drop down menu 634. Urgency drop down menu 632 provides the user to select high, medium, or low priority. Contact drop down menu 634 provides the user to choose the contact person, such as physician, nurse, or technician. Once all necessary information is added to request call back 630, save button 633 is selected and a "call back" message is sent to the chosen contact person.

Notes section 636 provides a text box for the user to enter text for the patient file. When no notes are attached to the patient file, there is a number zero next to the notes header. Once there is a note in the patient file, the number zero will change to a one and will continue to change as notes are subsequently added. Once a note is added in the text box, save button 637 is selected to save the note to the patient file.

Patient jacket 600 further includes review icon 638, study notes icon 640, telerad assistance icon 642, and call request icon 644. As previously discussed, review icon 638 indicates whether a study is ready for review. If a study is ready for review, then review icon 638 is highlighted one color, if not, it is highlighted a different color. Study notes icon 640 is highlighted in one color if there are any notes in the patient file for that study, if not, study notes icon 640 is highlighted a different color. Telerad assistance icon 642, if activated, is highlighted one color if the urgency is medium or routine, and highlighted a different color if the urgency is high, and indicates whether communication with the referring physician, nurse, or technologist has been requested by the user.

Call request icon 644 will be highlighted if a radiologist needs to return a phone call request to a physician, nurse, or technician.

Prior studies section 658 lists summaries of a patient's prior studies. The summaries include study assignment, date and time 664, image modality 666, exam type 668, location 670, medical record number 672, and study status 674. Prior studies section 658 also includes link buttons 662 to view prior study files or images for comparison. The summaries may be filtered by modality buttons 660. More than one modality button may be chosen and when chosen the prior study summaries for the chosen modalities will be listed.

Report summary section 676 displays exam type 678 and technique 680, as well as study findings 682 and impression 684.

Figure 7:
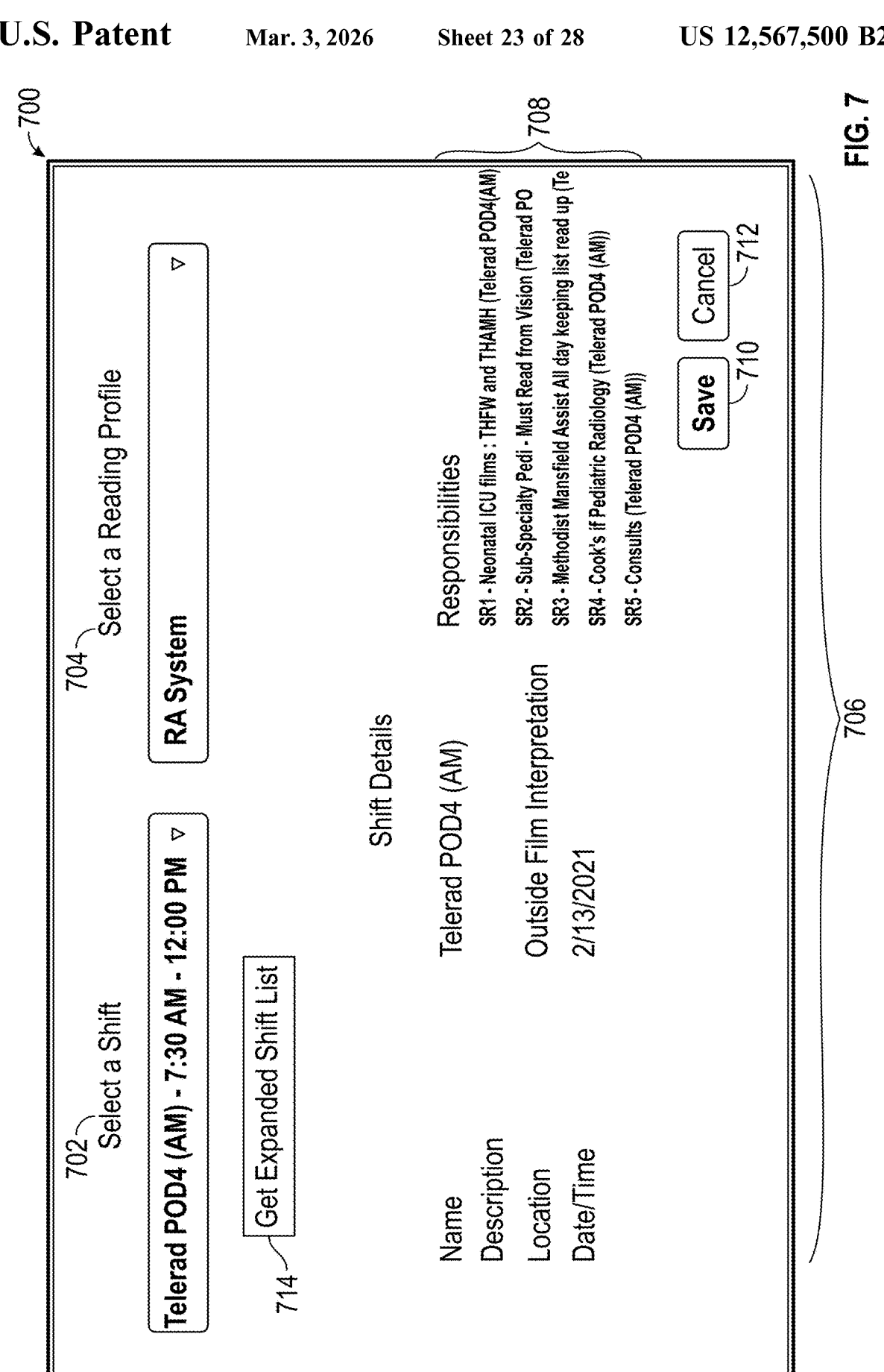
FIG. 7 is a screenshot of a graphic user interface of shift selection tab of a preferred embodiment.

Referring then to FIG. 7, shift selection box 700 will be further described.

Shift selection box 700 includes shift selection menu 702 and reading profile menu 704. When shift selection button 405 is selected, shift selection box 700 opens. Shift selection menu 702 is a drop-down menu and lists all available shifts. The user can choose any available shift. Reading profile menu 704 is also a drop-down menu and lists all available reading profiles from which a user can choose. A reading profile is the particular healthcare system, such as a hospital or other healthcare provider, from which studies will be pulled for review. Once a shift and reading profile are selected and save button 710 is selected, the worklist is filtered and updated to reflect all available unreviewed studies for that shift and reading profile.

Shift selection box 700 also includes shift details area 706 and shift responsibilities area 708. Shift details area 706 includes the name of the shift, description, location of the shift, and the date and time of the shift. Shift responsibilities area 708 includes all responsibilities associated with that particular shift, such as reviewing exams for a hospital's neonatal ICU or pediatric radiology department. Get expanded shift list button 714 functions to display all shifts for which the user is qualified. If a user does not wish to update the shift selection or reading profile, then cancel button 712 may be selected.

Figure 8:
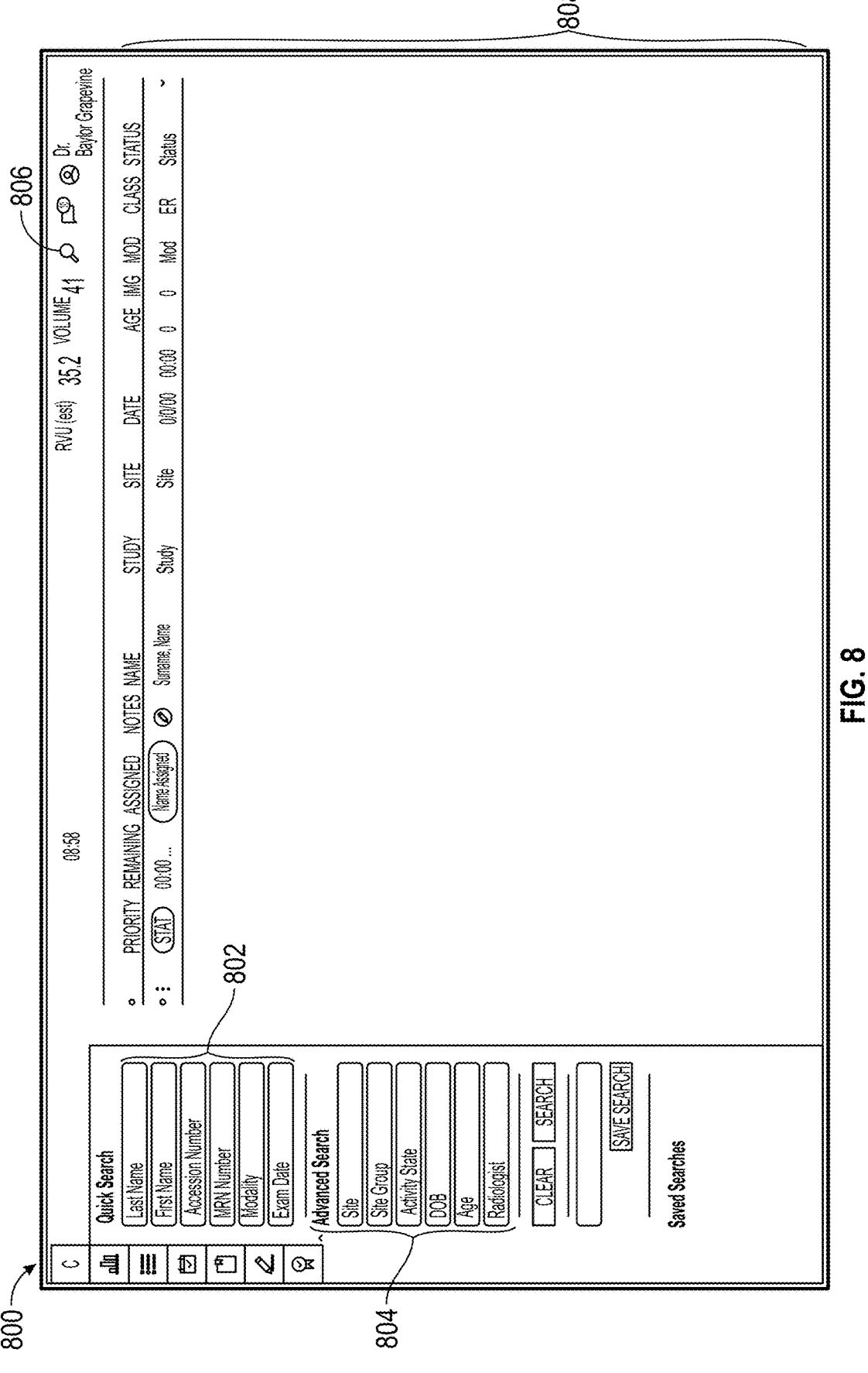
FIGS. 8 is a screenshot of a graphic user interface for a search function tab of a preferred embodiment.
Figure 9A:
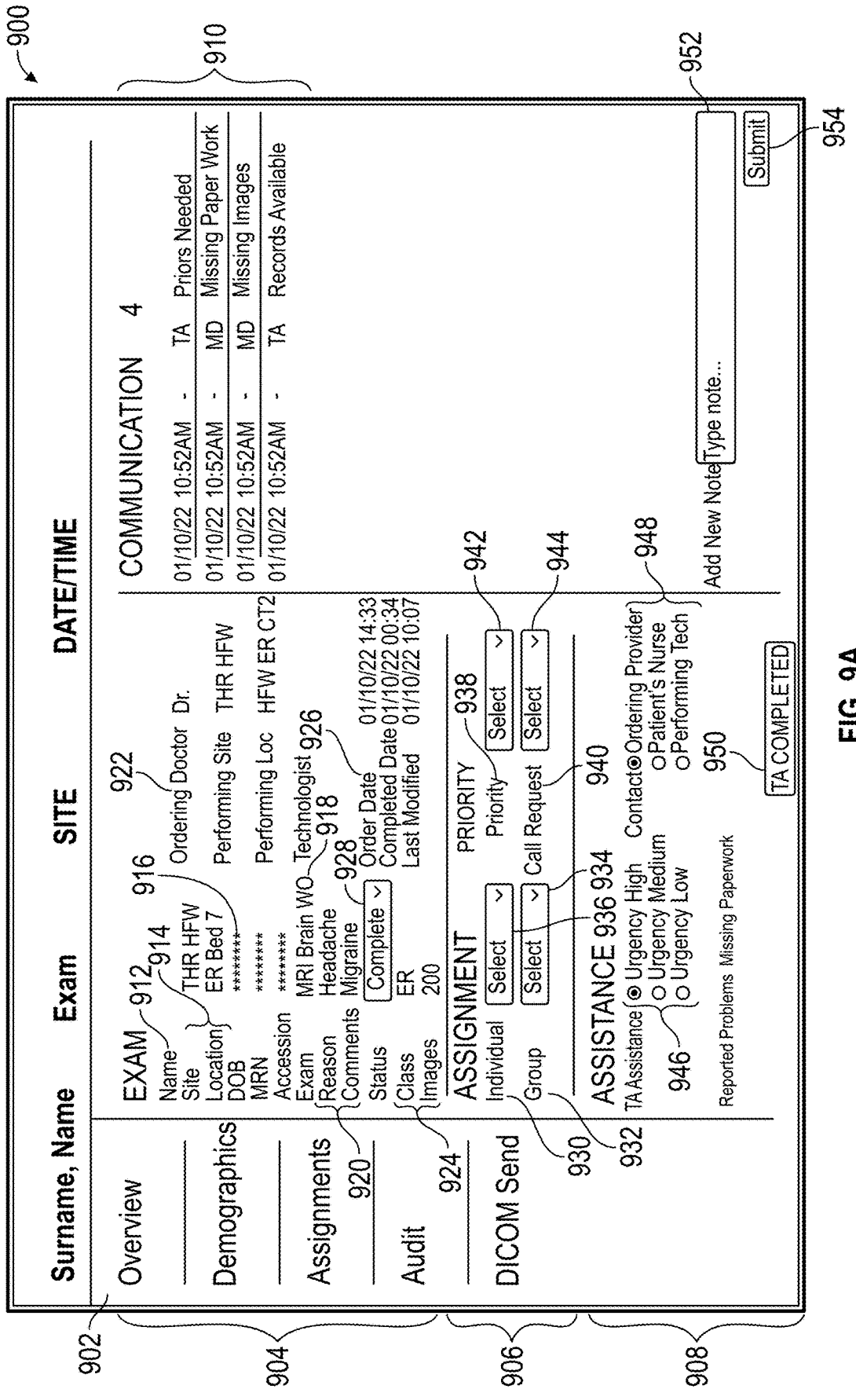
FIG. 9A is a screenshot of a graphic user interface for a study overview tab of a preferred embodiment.
Figure 9B:
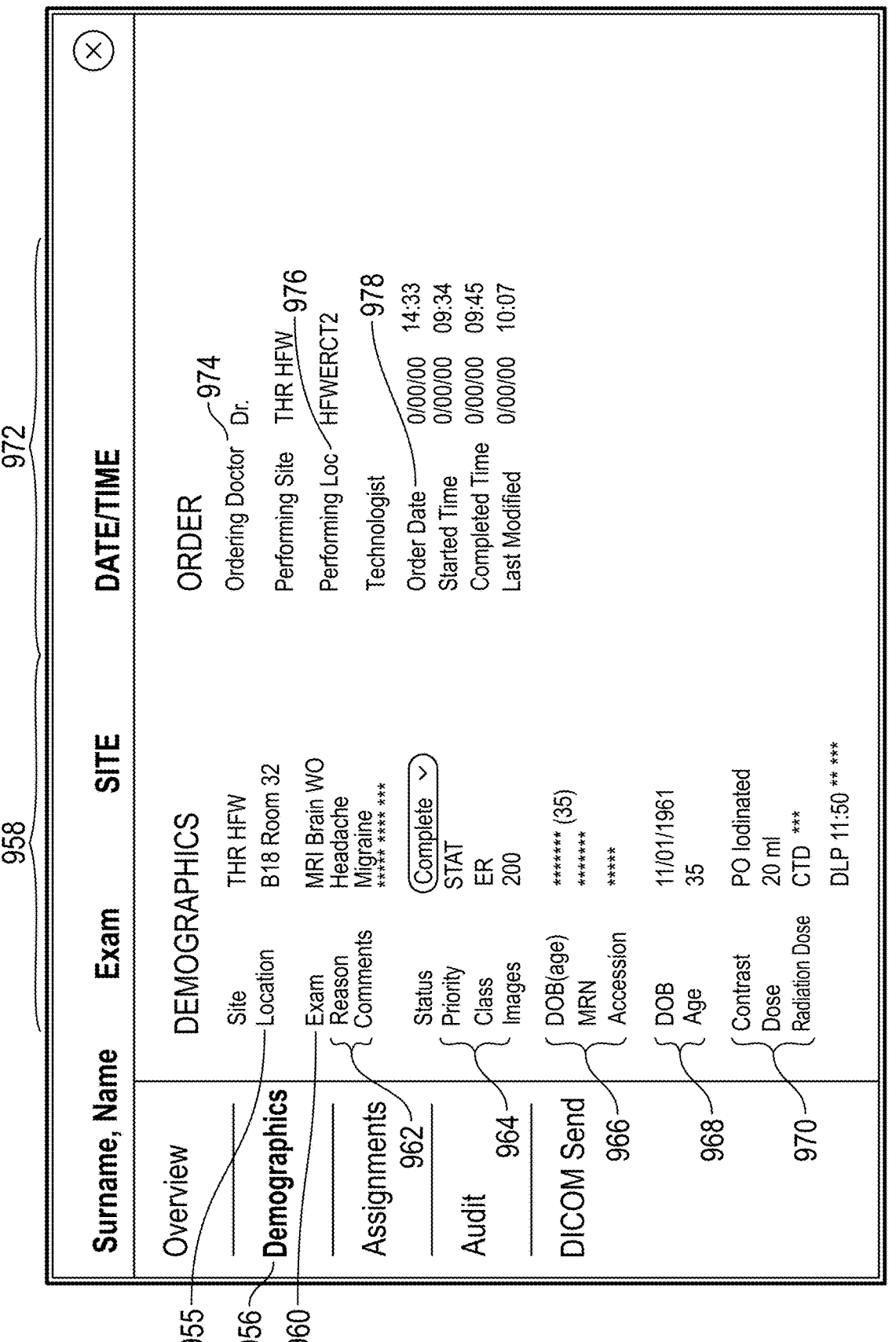
FIG. 9B is a screenshot of a graphic user interface for a demographics tab of a preferred embodiment.
Figure 9C:
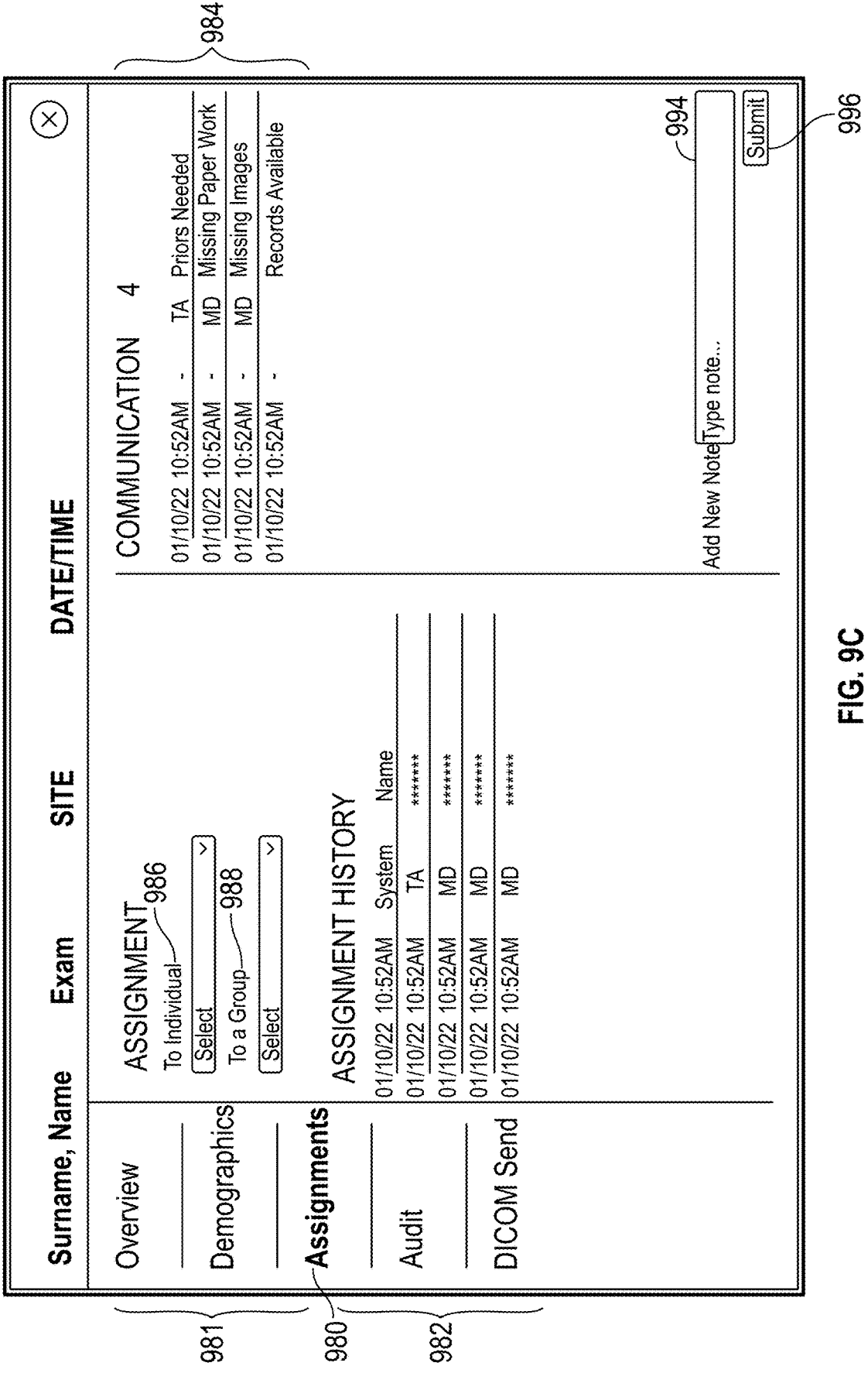
FIG. 9C is a screenshot of a graphic user interface for an assignment tab of a preferred embodiment.

Referring then to FIG. 8, a preferred graphic user interface of search screen 800 will be further described.

Quick search section 802 allows access to data based on a patient's name, medical record number, accession number, image modality, or exam date. Magnifying glass icon 806 presents a display of advanced search filters. Advanced search filters 804 allow access to data based on site, site group, activity state, date of birth, age, or user assigned. Once a user inputs the search information into quick search section 802 or advanced search filters 804, the relevant studies will be listed in study search list section 808.

Referring then to FIGS. 9A, 9B, 9C and 9D, screenshots of a graphic user interface for detailed views of study 900 will be further described. Detailed views of study 900 is accessed from worklist summary 400.

Overview tab 902 includes exam details section 904, assignment section 906, assistance section 908, and communication section 910.

Exam details section 904 includes information regarding the current exam, such as patient name 912, location 914, date of birth 916, exam type 918, reason for visit and comments 920, ordering physician 922, exam notes 924, order date information 926, and status dropdown 928. Status drop down 928 includes different indications for the study review process, such as review requested, pending, or complete.

Assignment section 906 includes details for individual 930 and group 932 assigned to the study, and details on priority 938 and call request 940. Individual 930, group 932, priority 938, and call request 940 may be modified using individual drop down 934, group drop down 936, priority drop down 942, and call request drop down 944.

Assistance section 908 allows the user to request assistance. The request must include urgency selection 946 and contact selection 948. When a request is submitted for assistance, completed button 950 is highlighted.

Communication section 910 shows all notes and communication added to the study. Communication section 910 also includes note text box 952 to submit additional notes to the study. Once a note is typed into note text box 952, submit button 954 is selected to add the note to the study.

Demographics tab 956 shows the demographics of the exam and the order request. Demographics column 958 for the exam includes details regarding exam location 955, exam type 960, reason and comments 962, priority and exam information 964, medical record numbers 966, patient information 968, and image type 970. Order column 972 includes requesting physician's information 974, performing location 976, and order date 978.

Assignment tab 980 includes assignment section 981, assignment history section 982, and communication history 984. Communication history 984 shows all notes added to the study. Assignment section 981 allows for assignment to an individual or group. The study assignment may be modified and reassigned using individual drop down 986 and group drop down 988. Assignment history section 982 shows all reassignments for the study. Communication history 984 also includes text box 994 and submit button 996 to type and to submit additional notes to the study.

Audit tab 997 shows summary column 998 of all edits made to the study, such as notes, assignments, and assistance requests. This tab is used to provide a summary of the study for productivity audits.

Detailed views of a study 900 also includes DICOM send tab 999. DICOM send tab 999 allows a user to easily transmit patient data and images to a non-ordering physician or medical facility, which ensures data and image continuity and integration when managing and communicating this information to the other physician or facility.

It will be appreciated by those skilled in the art that changes could be made to the embodiments described above without departing from the broad inventive concept. It is understood, therefore, that this disclosure is not limited to the particular embodiments herein, but it is intended to cover modifications within the spirit and scope of the present disclosure as defined by the appended claims.

The invention claimed is:

1. A method comprising:
improving distribution of radiology studies and efficient review of radiology studies based upon an automated analysis of a user by:
    providing an administrative server operatively connected to a network, and a database;
    generating a study upon accessing memory, at the administrative server, from an order and a set of images received at the administrative server;
    generating a worklist, comprising the study and a study priority of the study;
    sending the worklist from the administrative server to a client device of the user, responsive to a study list request from the client device;

providing a graphical user interface (GUI) at the client device, operatively connected to the network, and in communication with the administrative server;

displaying, at the GUI of the client device, a set of icons corresponding to a set of studies of the worklist, the set of icons comprising an icon for the study;

dynamically modifying characteristics of the set of icons on the GUI based upon a reprioritization of the set of studies of the worklist determined based upon a set of priority features;

receiving a study selection from the client device, sending, from the client device to a PACS, a first API call to display an image associated with the study selection, activating a dictation device upon sending, from the client device to a dictation device, a second API call to receive and log a dictation file; and at the administrative server and in coordination with sending the first API call and the second API call:

initiating a pendency clock and an elapsed time clock, and if the pendency clock reaches a timeout limit, causing a timeout message to be displayed at the client device, automatically closing the selected study at the client device, and storing a pendency time value of the pendency clock and an elapsed time value of the elapsed time clock, wherein modifying characteristics of the set of icons on the GUI based upon the reprioritization comprises automatically escalating a time elapsed icon, corresponding to the study selection, in the worklist if the elapsed time value reaches a threshold value.

2. The method of claim 1, further comprising returning a productivity metric for the user associated with the client device, upon receiving a request for user analytics through the GUI, wherein the productivity metric is determined from a number of studies reviewed within a time period indicated in the request.

3. The method of claim 1, further comprising reassigning the study from the user to a second user if the productivity metric for the user does not satisfy a condition.

4. The method of claim 3, wherein reassigning the study comprises removing the icon for the study from the GUI of the client device for the user, and positioning the icon for the study at a second GUI of a second client device for the second user.

5. The method of claim 3, further comprising reassigning the study based upon an evaluation of study urgency, radiologist availability, radiologist credentialing, and radiologist sub-specialization, determined for a set of users.

6. The method of claim 1, further comprising:

determining an elapsed time priority value (ETPV) from the elapsed time value and a modulus, determining a study priority number (SPN) for the study selection from the ETPV, and reordering the icons corresponding to the study list at the GUI based upon the SPV.

7. The method of claim 6, wherein generating the study priority number comprises determining: an urgency priority value of the study and a medical severity; and deriving the study priority based on the urgency priority value, the medical severity, and the elapsed time priority value.

8. The method of claim 7, wherein determining the physiology priority value comprises retrieving a physiology designation and assigning the physiology priority value based upon the physiology designation.

9. The method of claim 1, wherein providing the administrative server comprises providing a management application structured to coordinate communication with RIS systems and PACS systems.

10. The method of claim 1, further comprising displaying a set of images on the client device.

11. The method of claim 10, wherein the set of images comprises at least one of a set of radiological image types comprising an X-ray image, a CT image, an MRI image, a PET image, a mammography image, a DEXA scan, nuclear medicine imaging, and an ultrasound image.

12. The method of claim 1, wherein dynamically modifying positions of the set of icons of on the GUI comprises automatically moving the icon for the study to an updated position on the GUI ahead of the initial position on the GUI, based on the elapsed time.

13. The method of claim 1, wherein dynamically modifying characteristics of the set of icons on the GUI comprises modifying positions of the set of icons.

14. The method of claim 1, wherein dynamically modifying characteristics of the set of icons on the GUI comprises modifying colors of the set of icons.

15. A method comprising:

improving distribution of radiology studies and efficient review of radiology studies based upon an automated analysis of a user by:

providing an administrative server operatively connected to a network, and a database;

generating a study, upon accessing memory at the administrative server, from an order and a set of images received at the administrative server;

generating a worklist, comprising the study and a study priority of the study;

sending the worklist from the administrative server to a client device of the user, responsive to a study list request from the client device;

providing a graphical user interface (GUI) at the client device, operatively connected to the network, and in communication with the administrative server;

displaying, at the GUI of the client device, a set of icons corresponding to a set of studies of the worklist;

receiving, at the client device, a selection of the study;

modifying characteristics of the set of icons on the GUI in response to the selection;

locking the study for other users and initiating a pendency clock and an elapsed time clock, and if the pendency clock reaches a timeout limit, causing a timeout message to be displayed at the client device, automatically closing the study at the client device, and storing a pendency time value of the pendency clock and an elapsed time value of the elapsed time clock, wherein modifying characteristics of the set of icons on the GUI comprises automatically escalating a time elapsed icon, corresponding to the study, in the worklist if the elapsed time value reaches a threshold value.

16. The method of claim 15, further comprising returning a productivity metric for the user associated with the client device, upon receiving a request for user analytics through the GUI, wherein the productivity metric is determined from a number of studies reviewed within a time period indicated in the request.

17. The method of claim 16, reassigning the study to a second user if the pendency clock reaches the timeout limit, wherein reassigning the study comprises removing the icon for the study from the GUI of the client device for the user, and positioning the icon for the study at a second GUI of a second client device for the second user.

* * * * *